(12) United States Patent
Nissink et al.

(10) Patent No.: US 9,938,265 B2
(45) Date of Patent: Apr. 10, 2018

(54) 1,3,4-THIADIAZOLE COMPOUNDS AND THEIR USE IN TREATING CANCER

(71) Applicants: AstraZeneca AB, Sodertalje (SE); Cancer Research Technology Limited, London (GB)

(72) Inventors: Johannes Wilhelmus Maria Nissink, Cambridge (GB); Maurice Raymond Verschoyle Finlay, Cambridge (GB); Mark David Charles, Cambridge (GB); Matt Wood, Macclesfiled (GB)

(73) Assignees: AstraZeneca AB (SE); Cancer Research Technology Limited (GB)

( * ) Notice: Subject to any disclaimer, the term of this patent is extended or adjusted under 35 U.S.C. 154(b) by 0 days.

(21) Appl. No.: 15/363,018

(22) Filed: Nov. 29, 2016

(65) Prior Publication Data

US 2017/0152254 A1 Jun. 1, 2017

Related U.S. Application Data

(60) Provisional application No. 62/260,787, filed on Nov. 30, 2015.

(51) Int. Cl.
*C07D 417/14* (2006.01)
(52) U.S. Cl.
CPC .................. *C07D 417/14* (2013.01)
(58) Field of Classification Search
CPC .................................................. C07D 417/14
See application file for complete search history.

(56) References Cited

U.S. PATENT DOCUMENTS

| | | | | |
|---|---|---|---|---|
| 6,642,237 B1 * | 11/2003 | Tata | ...................... | A61K 31/00 514/252.02 |
| 7,683,063 B2 * | 3/2010 | Kyle | .................... | C07D 211/78 514/247 |
| 8,003,806 B2 * | 8/2011 | Bloxham | ............. | C07D 235/06 544/182 |
| 2010/0267722 A1 * | 10/2010 | Sanchez | ............... | C07D 207/16 514/235.5 |
| 2014/0142081 A1 | 5/2014 | Lemieux et al. | | |

FOREIGN PATENT DOCUMENTS

| WO | 2013078123 A1 | 5/2013 |
|---|---|---|
| WO | 2015181539 A1 | 12/2015 |
| WO | 2017093299 A1 | 6/2017 |
| WO | 2017093301 A1 | 6/2017 |

OTHER PUBLICATIONS

Ajit, G., et al., "Small molecule glutaminase inhibitors block glutamate release from stimulated microglia", Biochemical and Biophysical Research Communications, Jan. 1, 2014, vol. 443, No. 1, pp. 32-36.

* cited by examiner

*Primary Examiner* — Kamal Saeed
(74) *Attorney, Agent, or Firm* — Daniel Kopp

(57) ABSTRACT

A compound of Formula (I):

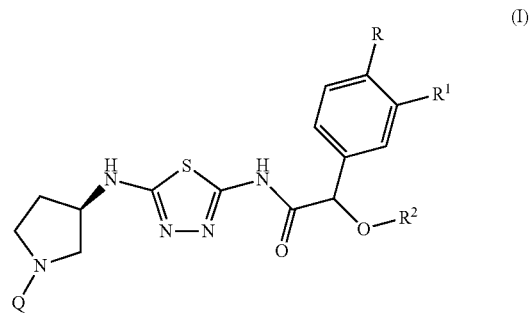

or a pharmaceutically acceptable salt thereof, where: Q can be 5-methylpyridazin-3-yl,5-chloropyridazin-3-yl, 6-methylpyridazin-3-yl, or 6-fluoropyridazin-3-yl; R can be hydrogen, fluoro, or methoxy; $R^1$ can be hydrogen, methoxy, difluoromethoxy, or trifluoromethoxy; and $R^2$ can be methyl or ethyl. The compound of formula (I) can inhibit glutaminase, e.g., GLS1.

9 Claims, No Drawings

1,3,4-THIADIAZOLE COMPOUNDS AND THEIR USE IN TREATING CANCER

CROSS-REFERENCE TO RELATED APPLICATIONS

This application claims the benefit under 35 U.S.C. § 119(e) to U.S. application Ser. No. 62/260,787 filed on 30 Nov. 2015, the entirety of which is hereby incorporated by reference.

TECHNICAL FIELD

The specification generally relates to substituted 1,3,4-thiadiazole compounds and pharmaceutically acceptable salts thereof. These compounds act on the glutaminase 1 enzyme ("GLS1"), and the specification therefore also relates to the use of such compounds and salts thereof to treat or prevent GLS1-mediated disease, including cancer. The specification further relates pharmaceutical compositions comprising such compounds and salts; kits comprising such compounds and salts; methods of manufacture of such compounds and salts; intermediates useful in the manufacture of such compounds and salts; and to methods of treating GLS1 mediated disease, including cancer, using such compounds and salts.

BACKGROUND

Glutamine is the most abundant plasma amino acid and is involved in many growth promoting pathways. In particular, glutamine is involved in oxidation in the TCA cycle and in maintaining cell redox equilibrium, and also provides nitrogen for nucleotide and amino acid synthesis (Curi et al., *Front. Biosci.* 2007, 12, 344-57; DeBerardinis and Cheng, *Oncogene* 2010, 313-324, each of which is incorporated by reference in its entirety). Many cancer cells rely on glutamine metabolism as a consequence of metabolic changes in the cell, including the Warburg effect where glycolytic pyruvate is converted to lactic acid rather than being used to create acetyl CoA (Koppenol et al., *Nature Reviews* 2011, 11, 325-337, which is incorporated by reference in its entirety). As a consequence of this reliance on glutamine metabolism, such cancer cells are sensitive to changes in exogenous glutamine levels. Furthermore, existing evidence suggests that glutaminolysis plays a key role in certain cancer types (Hensley et al., *J. Clin. Invest.* 2013, 123, 3678-3684, which is incorporated by reference in its entirety), and is associated with known oncogenic drivers such as Myc (Dang, *Cancer Res.* 2010, 70, 859-863, which is incorporated by reference in its entirety).

The first step of glutamine catabolism to glutamate is catalysed by glutaminase, which exists as two isoforms, GLS1 and GLS2, originally identified as being expressed in the kidney and liver, respectively. Kidney glutaminase (GLS1) is known to be more ubiquitously expressed than liver glutaminase (GLS2), and has 2 splice variants, KGA and the shorter GAC isoform, both of which are located in the mitochondria. (Elgadi et al., *Physiol. Genomics* 1999, 1, 51-62; Cassago et al., *Proc. Natl. Acad. Sci.* 2012, 109, 1092-1097, each of which is incorporated by reference in its entirety). GLS1 expression is associated with tumour growth and malignancy in a number of disease types (Wang et al., *Cancer Cell* 2010, 18, 207-219; van der Heuval et al., *Cancer Bio. Ther.* 2012, 13, 1185-1194, each of which is incorporated by reference in its entirety). Inhibitors of GLS1 are therefore expected to be useful in the treatment of cancer, as monotherapy or in combination with other anti-cancer agents.

SUMMARY

In one aspect, a compound of Formula (I):

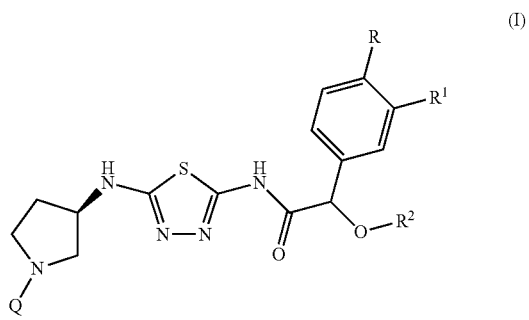

or a pharmaceutically acceptable salt thereof, where:

Q is 5-methylpyridazin-3-yl, 5-chloropyridazin-3-yl, 6-methylpyridazin-3-yl, or 6-fluoropyridazin-3-yl;

R is hydrogen, fluoro, or methoxy;

$R^1$ is hydrogen, methoxy, difluoromethoxy, or trifluoromethoxy; and $R^2$ is methyl or ethyl.

In another aspect, a pharmaceutical composition includes the compound of Formula (I), or a pharmaceutically acceptable salt thereof, and at least one pharmaceutically acceptable diluent or carrier.

In another aspect, the compound of Formula (I), or a pharmaceutically acceptable salt thereof, for use in therapy.

In another aspect, the compound of Formula (I), or a pharmaceutically acceptable salt thereof, for use in the treatment of cancer.

In another aspect, use of the compound of Formula (I), or a pharmaceutically acceptable salt thereof, for the manufacture of a medicament for the treatment of cancer.

In another aspect, a method for treating cancer in a warm blooded animal in need of such treatment, includes administering to the warm-blooded animal a therapeutically effective amount of a compound of Formula (I), or a pharmaceutically acceptable salt thereof.

Other aspects will be apparent from the specification and the claims.

DETAILED DESCRIPTION

Many embodiments are detailed throughout the specification and will be apparent to a reader skilled in the art. The invention is not to be interpreted as being limited to any particular embodiment(s) thereof.

A compound of Formula (I) is provided:

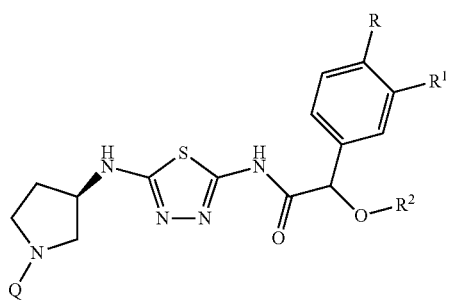

or a pharmaceutically acceptable salt thereof, where:

Q is 5-methylpyridazin-3-yl, 5-chloropyridazin-3-yl, 6-methylpyridazin-3-yl, or 6-fluoropyridazin-3-yl;

R is hydrogen, fluoro, or methoxy;

$R^1$ is hydrogen, methoxy, difluoromethoxy, or trifluoromethoxy; and $R^2$ is methyl or ethyl.

5-methylpyridazin-3-yl, 5-chloropyridazin-3-yl, 6-methylpyridazin-3-yl, or 6-fluoropyridazin-3-yl rings have the following structures:

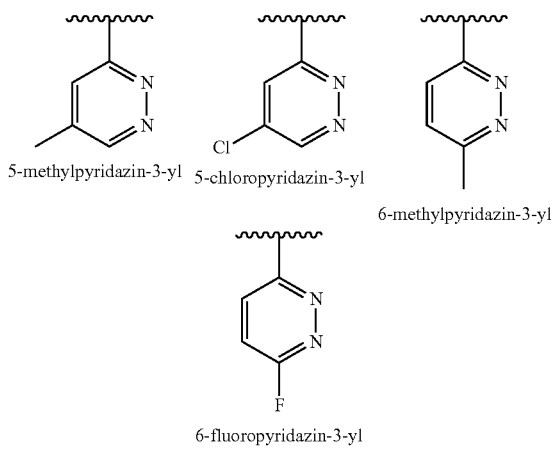

In some embodiments, the compound of Formula (I) has the following Formula (Ia):

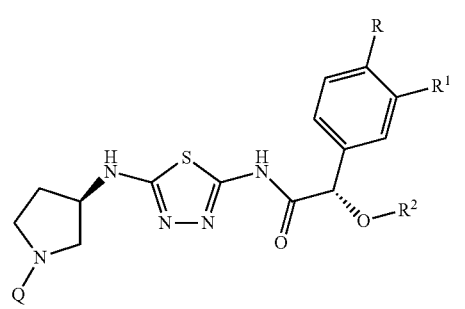

wherein Q, R, $R^1$, and $R^2$ are defined as above.

The term "pharmaceutically acceptable" is used to specify that an object (for example a salt, dosage form, diluent or carrier) is suitable for use in patients. An example list of pharmaceutically acceptable salts can be found in the *Handbook of Pharmaceutical Salts: Properties, Selection and Use*, P. H. Stahl and C. G. Wermuth, editors, Weinheim/Zürich: Wiley-VCH/VHCA, 2002, which is incorporated by reference in its entirety. A suitable pharmaceutically acceptable salt of a compound of Formula (I) is, for example, an acid-addition salt. An acid addition salt of a compound of Formula (I) may be formed by bringing the compound into contact with a suitable inorganic or organic acid under conditions known to the skilled person. An acid addition salt may be formed using, for example, an inorganic acid such as hydrochloric acid, hydrobromic acid, sulphuric acid, and phosphoric acid. An acid addition salt may also be formed using, for example, an organic acid such as trifluoroacetic acid, methanesulfonic acid, or benzenesulfonic acid.

Therefore, in one embodiment there is provided a compound of Formula (I) or a pharmaceutically acceptable salt thereof, where the pharmaceutically acceptable salt is a hydrochloric acid, hydrobromic acid, sulphuric acid, phosphoric acid, trifluoroacetic acid, methanesulfonic acid, or benzenesulfonic acid salt.

In one embodiment there is provided a compound of Formula (I) or a pharmaceutically acceptable salt thereof, where the pharmaceutically acceptable salt is a hydrochloric acid or hydrobromic acid salt.

A further suitable pharmaceutically acceptable salt of a compound of Formula (I) is a base-addition salt. A base addition salt of a compound of Formula (I) may be formed by bringing the compound into contact with a suitable inorganic or organic base under conditions known to the skilled person. A base addition salt may for example be formed using, for example, an inorganic base such as an alkali metal hydroxide (such as sodium, potassium, or lithium hydroxide) or an alkaline earth metal hydroxide (such as calcium hydroxide or magnesium hydroxide). A base addition salt may also be formed using, for example, an organic base such as methylamine, dimethylamine, trimethylamine, piperidine, morpholine, or tris-(2-hydroxyethyl)amine.

Therefore, in one embodiment there is provided a compound of Formula (I) or a pharmaceutically acceptable salt thereof, where the pharmaceutically acceptable salt is a sodium hydroxide, potassium hydroxide, lithium hydroxide, calcium hydroxide, magnesium hydroxide, methylamine, dimethylamine, trimethylamine, piperidine, morpholine, or tris-(2-hydroxyethyl)amine salt.

In one embodiment there is provided a compound of Formula (I) or a pharmaceutically acceptable salt thereof, where the pharmaceutically acceptable salt is a hydrochloric acid, hydrobromic acid, sulphuric acid, phosphoric acid, trifluoroacetic acid, methanesulfonic acid, benzenesulfonic acid, sodium hydroxide, potassium hydroxide, lithium hydroxide, calcium hydroxide, magnesium hydroxide, methylamine, dimethylamine, trimethylamine, piperidine, morpholine, or tris-(2-hydroxyethyl)amine salt.

A further embodiment provides any of the embodiments defined herein (for example the embodiment of claim 1) with the proviso that one or more specific Examples (for instance one, two or three specific Examples, or alternatively one specific Example) selected from the group consisting of Examples 1(a), 1(b), 2, 3, 4(a), 4(b), 5(a), 5(b), 6(a), 6(b), 7(a), 7(b), 8(a), 8(b), 9(a), 9(b), 10(a), 10(b), 11(a), 11(b), 12, 13, 14, 15, 16, 17, 18, 19, 20, 21, 22, 23, 24, 25, 26 27, 28, 29, 30, 31, 32, 33(a), and 33(b) is individually disclaimed.

Some values of variable groups in Formula (I) are as follows. Such values may be used in combination with any of the definitions, claims (for example claim 1), or embodiments defined herein to provide further embodiments.

Q can be 6-methylpyridazin-3-yl or 6-fluoropyridazin-3-yl.

Q can be 5-methylpyridazin-3-yl or 5-chloropyridazin-3-yl.

Q can be 5-methylpyridazin-3-yl.
Q can be 5-chloropyridazin-3-yl.
Q can be 6-methylpyridazin-3-yl.
Q can be or 6-fluoropyridazin-3-yl.
R can be hydrogen or fluoro.
R can be hydrogen.
$R^1$ can be methoxy, difluoromethoxy, or trifluoromethoxy.
$R^2$ can be methyl.

In one embodiment there is provided a compound of Formula (I), or a pharmaceutically acceptable salt thereof, where:
Q is 6-methylpyridazin-3-yl or 6-fluoropyridazin-3-yl; and
$R^1$ is methoxy or trifluoromethoxy.

In one embodiment there is provided a compound of Formula (I), or a pharmaceutically acceptable salt thereof, where:
Q is 6-methylpyridazin-3-yl or 6-fluoropyridazin-3-yl;
R is hydrogen; and
$R^1$ is methoxy or trifluoromethoxy.

In one embodiment there is provided a compound of Formula (I), or a pharmaceutically acceptable salt thereof, where:
Q is 6-methylpyridazin-3-yl or 6-fluoropyridazin-3-yl;
R is hydrogen;
$R^1$ is methoxy or trifluoromethoxy; and
$R^2$ is methyl.

In one embodiment there is provided a compound of Formula (I), or a pharmaceutically acceptable salt thereof, where:
Q is 6-methylpyridazin-3-yl or 6-fluoropyridazin-3-yl; and
R is fluoro.

In one embodiment there is provided a compound of Formula (I), or a pharmaceutically acceptable salt thereof, where the compound is selected from the group consisting of:
(2S)-2-methoxy-2-(3-methoxyphenyl)-N-[5-[[(3R)-1-(6-methylpyridazin-3-yl)pyrrolidin-3-yl]amino]-1,3,4-thiadiazol-2-yl]acetamide;
(2S)-N-[5-[[(3R)-1-(6-fluoropyridazin-3-yl)pyrrolidin-3-yl]amino]-1,3,4-thiadiazol-2-yl]-2-methoxy-2-phenyl-acetamide;
(2S)-N-[5-[[(3R)-1-(6-fluoropyridazin-3-yl)pyrrolidin-3-yl]amino]-1,3,4-thiadiazol-2-yl]-2-methoxy-2-(3-methoxyphenyl)acetamide;
(2S)-2-ethoxy-2-(3-methoxyphenyl)-N-[5-[[(3R)-1-(6-methylpyridazin-3-yl)pyrrolidin-3-yl]amino]-1,3,4-thiadiazol-2-yl]acetamide;
(2S)-2-(4-fluorophenyl)-2-methoxy-N-[5-[[(3R)-1-(6-methylpyridazin-3-yl)pyrrolidin-3-yl]amino]-1,3,4-thiadiazol-2-yl]acetamide;
(2S)-2-(4-fluoro-3-methoxy-phenyl)-2-methoxy-N-[5-[[(3R)-1-(6-methylpyridazin-3-yl)pyrrolidin-3-yl]amino]-1,3,4-thiadiazol-2-yl]acetamide;
(2S)-2-methoxy-N-[5-[[(3R)-1-(6-methylpyridazin-3-yl)pyrrolidin-3-yl]amino]-1,3,4-thiadiazol-2-yl]-2-[3-(trifluoromethoxy)phenyl]acetamide;
(2S)-2-(4-fluorophenyl)-2-methoxy-N-[5-[[(3R)-1-(5-methylpyridazin-3-yl)pyrrolidin-3-yl]amino]-1,3,4-thiadiazol-2-yl]acetamide;
N-[5-[[(3R)-1-(5-chloropyridazin-3-yl)pyrrolidin-3-yl]amino]-1,3,4-thiadiazol-2-yl]-2-methoxy-2-(4-methoxyphenyl)acetamide;
(2S)-[3-(difluoromethoxy)phenyl]-2-methoxy-N-[5-[[(3R)-1-(6-methylpyridazin-3-yl)pyrrolidin-3-yl]amino]-1,3,4-thiadiazol-2-yl]acetamide; and
(2S)-2-[3-(difluoromethoxy)phenyl]-N-[5-[[(3R)-1-(6-fluoropyridazin-3-yl)pyrrolidin-3-yl]amino]-1,3,4-thiadiazol-2-yl]-2-methoxy-acetamide.

In one embodiment there is provided a compound of Formula (I), or a pharmaceutically acceptable salt thereof, where the compound is selected from the group consisting of:
(2S)-2-methoxy-2-(3-methoxyphenyl)-N-[5-[[(3R)-1-(6-methylpyridazin-3-yl)pyrrolidin-3-yl]amino]-1,3,4-thiadiazol-2-yl]acetamide;
(2S)-N-[5-[[(3R)-1-(6-fluoropyridazin-3-yl)pyrrolidin-3-yl]amino]-1,3,4-thiadiazol-2-yl]-2-methoxy-2-(3-methoxyphenyl)acetamide;
(2S)-2-ethoxy-2-(3-methoxyphenyl)-N-[5-[[(3R)-1-(6-methylpyridazin-3-yl)pyrrolidin-3-yl]amino]-1,3,4-thiadiazol-2-yl]acetamide;
(2S)-2-(4-fluorophenyl)-2-methoxy-N-[5-[[(3R)-1-(6-methylpyridazin-3-yl)pyrrolidin-3-yl]amino]-1,3,4-thiadiazol-2-yl]acetamide;
(2S)-2-(4-fluoro-3-methoxy-phenyl)-2-methoxy-N-[5-[[(3R)-1-(6-methylpyridazin-3-yl)pyrrolidin-3-yl]amino]-1,3,4-thiadiazol-2-yl]acetamide;
(2S)-2-methoxy-N-[5-[[(3R)-1-(6-methylpyridazin-3-yl)pyrrolidin-3-yl]amino]-1,3,4-thiadiazol-2-yl]-2-[3-(trifluoromethoxy)phenyl]acetamide;
(2S)-2-(4-fluorophenyl)-2-methoxy-N-[5-[[(3R)-1-(5-methylpyridazin-3-yl)pyrrolidin-3-yl]amino]-1,3,4-thiadiazol-2-yl]acetamide;
(2S)-[3-(difluoromethoxy)phenyl]-2-methoxy-N-[5-[[(3R)-1-(6-methylpyridazin-3-yl)pyrrolidin-3-yl]amino]-1,3,4-thiadiazol-2-yl]acetamide; and
(2S)-2-[3-(difluoromethoxy)phenyl]-N-[5-[[(3R)-1-(6-fluoropyridazin-3-yl)pyrrolidin-3-yl]amino]-1,3,4-thiadiazol-2-yl]-2-methoxy-acetamide.

Compounds and salts described in this specification may exist in solvated forms and unsolvated forms. For example, a solvated form may be a hydrated form, such as a hemihydrate, a mono-hydrate, a di-hydrate, a tri-hydrate or an alternative quantity thereof. The present invention encompasses all such solvated and unsolvated forms of compounds of Formula (I).

Atoms of the compounds and salts described in this specification may exist in different isotopic forms. The present invention encompasses all isotopic forms of compounds of Formula (I) including an $^{11}C$ or $^{13}C$ carbon and $^{1}H$, $^{2}H$ (deuterium) or $^{3}H$ (tritium)hydrogen.

Compounds and salts described in this specification may exist as a mixture of tautomers. "Tautomers" are structural isomers that exist in equilibrium resulting from the migration of a hydrogen atom. The present invention includes all tautomers of compounds of Formula (I).

Compounds of Formula (I) can be prepared in different diastereomeric forms. The present invention includes all diastereomeric forms of the compounds of Formula (I).

In one embodiment there is provided a compound of Formula (I), or a pharmaceutically acceptable salt thereof, which is a single diastereomer being in an diastereomeric excess (% de) of ≥95%, ≥98% or ≥99%. In one embodiment, the single diastereomer is present in diastereomeric excess (% de) of ≥99%.

Compounds believed to inhibit GLS1, i.e., the compounds of Formula (I), and pharmaceutically acceptable salts thereof are expected to be useful in therapy, for example in the treatment of diseases or medical conditions mediated at least in part by GLS1, including cancer.

Where "cancer" is mentioned, this includes both non-metastatic cancer and also metastatic cancer, such that treating cancer involves treatment of both primary tumours and also tumour metastases.

In one embodiment the cancer is metastatic cancer.

In one embodiment the cancer is non-metastatic cancer.

"GLS1 inhibitory activity" refers to a decrease in the activity of GLS1 as a direct or indirect response to the presence of a compound of Formula (I), or pharmaceutically acceptable salt thereof, relative to the activity of GLS1 in the absence of compound of Formula (I), or pharmaceutically acceptable salt thereof. Such a decrease in activity may be due to the direct interaction of the compound of Formula (I), or pharmaceutically acceptable salt thereof with GLS1, or due to the interaction of the compound of Formula (I), or pharmaceutically acceptable salt thereof with one or more other factors that in turn affect GLS1 activity. For example, the compound of Formula (I), or pharmaceutically acceptable salt thereof, may decrease GLS1 by directly binding to GLS1; by causing (directly or indirectly) another factor to decrease GLS1 activity; or by (directly or indirectly) decreasing the amount of GLS1 present in the cell or organism.

The term "therapy" is intended to have its normal meaning of treating a disease or correcting or compensating for the underlying pathology. The term "therapy" also includes "prophylaxis" unless there are specific indications to the contrary. The terms "therapeutic" and "therapeutically" should be interpreted in a corresponding manner.

The term "therapeutically effective amount" refers to an amount of a compound of Formula (I) as described in any of the embodiments herein which is effective to provide therapy in a subject. In the case of cancer, the therapeutically effective amount may cause any of the changes observable or measurable in a subject as described in the definition of "therapy", "treatment" and "prophylaxis" above. For example, the effective amount can reduce the number of cancer or tumor cells; reduce the overall tumor size; inhibit or stop tumor cell infiltration into peripheral organs including, for example, the soft tissue and bone; inhibit and stop tumor metastasis; inhibit and stop tumor growth; relieve to some extent one or more of the symptoms associated with the cancer; reduce morbidity and mortality; improve quality of life; or a combination of such effects. An effective amount may be an amount sufficient to decrease the symptoms of a disease responsive to inhibition of GLS1 activity. For cancer therapy, efficacy in-vivo can, for example, be measured by assessing the duration of survival, time to disease progression (TTP), the response rates (RR), duration of response, and/or quality of life. As recognized by those skilled in the art, effective amounts may vary depending on route of administration, excipient usage, and co-usage with other agents. For example, where a combination therapy is used, the amount of the compound of Formula (I) or pharmaceutically acceptable salt described in this specification and the amount of the other pharmaceutically active agent(s) are, when combined, jointly effective to treat a targeted disorder in the animal patient. In this context, the combined amounts are in a "therapeutically effective amount" if they are, when combined, sufficient to decrease the symptoms of a disease responsive to inhibition of GLS1 activity as described above. Typically, such amounts may be determined by one skilled in the art by, for example, starting with the dosage range described in this specification for the compound of Formula (I) or pharmaceutically acceptable salt thereof and an approved or otherwise published dosage range(s) of the other pharmaceutically active compound(s).

The term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease.

The term "treatment" is used synonymously with "therapy". Similarly the term "treat" can be regarded as applying therapy where "therapy" is as defined herein.

In one embodiment there is provided a pharmaceutical composition including the compound of Formula (I), or a pharmaceutically acceptable salt thereof, and at least one pharmaceutically acceptable diluent or carrier. In one embodiment, the pharmaceutical composition includes a compound of Formula (I) as a free base. In another embodiment, the pharmaceutical composition includes a a pharmaceutically acceptable salt of a compound of Formula (I).

In one embodiment there is provided a compound of Formula (I), or a pharmaceutically acceptable salt thereof, for use in therapy.

In one embodiment there is provided a compound of Formula (I), or a pharmaceutically acceptable salt thereof, for use in the treatment of cancer.

In one embodiment there is provided the use of the compound of Formula (I), or a pharmaceutically acceptable salt thereof, for the manufacture of a medicament for the treatment of cancer.

In one embodiment there is provided a compound of Formula (I), or a pharmaceutically acceptable salt thereof, for use in the treatment of a disease mediated by GLS1. In one embodiment, the disease mediated by GLS1 is cancer. In some embodiments, the cancer can be breast cancer (for example triple negative breast cancer), lung cancer (for example non-small cell lung cancer), pancreatic cancer, renal cancer, or hepatocellular cancer.

"Triple negative breast cancer" is any breast cancer that does not express, or underexpresses, the genes for the estrogen receptor, progesterone receptor and Her2/neu.

In one embodiment there is provided the use of the compound of Formula (I), or a pharmaceutically acceptable salt thereof, for the manufacture of a medicament for the treatment of a disease mediated by GLS1. In one embodiment, the disease mediated by GLS1 is cancer. In some embodiments, the cancer can be breast cancer (for example triple negative breast cancer), lung cancer (for example non-small cell lung cancer), pancreatic cancer, renal cancer, or hepatocellular cancer.

In one embodiment there is provided the use of the compound of Formula (I), or a pharmaceutically acceptable salt thereof, for the manufacture of a medicament for the treatment of cancer.

In one embodiment there is provided a method of inhibiting GLS1 which includes administering a compound of Formula (I).

In one embodiment there is provided a method for treating a disease in which inhibition of GLS1 is beneficial in a warm-blooded animal in need of such treatment, which includes administering to the warm-blooded animal a therapeutically effective amount of a compound of Formula (I), or a pharmaceutically acceptable salt thereof.

"Warm-blooded animals" include, for example, humans.

In one embodiment there is provided a method for treating cancer in a warm-blooded animal in need of such treatment, which includes administering to the warm-blooded animal a therapeutically effective amount of a compound of Formula (I), or a pharmaceutically acceptable salt thereof. In some embodiments, the cancer can be breast cancer (for example triple negative breast cancer), lung cancer (for example non-small cell lung cancer), pancreatic cancer, renal cancer, or hepatocellular cancer.

The treatment for cancer described in this specification may be applied as a sole therapy, or may involve, in addition to administration of the compound of Formula (I), conventional surgery, radiotherapy, or chemotherapy; or a combination of such additional therapies. Such conventional surgery, radiotherapy, or chemotherapy may be administered simultaneously, sequentially, or separately to treatment with the compound of Formula (I).

Therefore, in one embodiment there is provided a compound of Formula (I), or a pharmaceutically acceptable salt thereof, and at least one additional anti-tumour substance, for use in the treatment of cancer.

In one embodiment there is provided a compound of Formula (I), or a pharmaceutically acceptable salt thereof, and at least one additional anti-tumour substance for use in the simultaneous, separate or sequential treatment of cancer.

In one embodiment there is provided a compound of Formula (I), or a pharmaceutically acceptable salt thereof, for use in the treatment of cancer, where the compound of Formula (I) is administered simultaneously, separately, or sequentially with at least one additional anti-tumour substance.

In one embodiment there is provided a method of treating cancer in a warm-blooded animal who is in need of such treatment, which includes administering to the warm-blooded animal a compound of Formula (I), or a pharmaceutically acceptable salt thereof and at least one additional anti-tumour substance, wherein the amounts of the compound of Formula (I), or a pharmaceutically acceptable salt thereof, and the additional anti-tumour substance are jointly effective in producing an anti-cancer effect.

In one embodiment there is provided a method of treating cancer in a warm-blooded animal who is in need of such treatment, which includes administering to the warm-blooded animal a compound of Formula (I), or a pharmaceutically acceptable salt thereof, and simultaneously, separately or sequentially administering at least one additional anti-tumour substance to the warm-blooded animal, wherein the amounts of the compound of Formula (I), or pharmaceutically acceptable salt thereof, and the additional anti-tumour substance are jointly effective in producing an anti-cancer effect.

In any embodiment the additional anti-tumour substance is a taxane. In one embodiment the taxane is paclitaxel. In one embodiment the taxane is docetaxel.

In any embodiment the additional anti-tumour substance is a platinum therapy. In one embodiment the platinum therapy is cisplatin, oxaliplatin, or carboplatin.

According to a further embodiment there is provided a kit comprising:
a) A compound of Formula (I), or a pharmaceutically acceptable salt thereof, in a first unit dosage form;
b) A second anti-tumour substance in a second unit dosage form;
c) A container for containing the first and second unit dosage forms; and, optionally,
d) Instructions for use.

The compounds of Formula (I), and pharmaceutically acceptable salts thereof, may be administered as pharmaceutical compositions, comprising one or more pharmaceutically acceptable diluents or carriers. Accordingly, in one embodiment there is provided a pharmaceutical composition comprising a compound of Formula (I), or a pharmaceutically acceptable salt thereof, and at least one pharmaceutically acceptable diluent or carrier.

The compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular dosing), or as a suppository. The compositions may be obtained by conventional procedures using conventional pharmaceutical excipients. Thus, compositions intended for oral use may contain, for example, one or more coloring, sweetening, flavoring, and/or preservative agents.

In one embodiment there is provided a pharmaceutical composition comprising a compound of Formula (I), or a pharmaceutically acceptable salt thereof, and at least one pharmaceutically acceptable diluent or carrier, for use in therapy.

In one embodiment there is provided a pharmaceutical composition comprising a compound of Formula (I), or a pharmaceutically acceptable salt thereof, and at least one pharmaceutically acceptable diluent or carrier, for use in the treatment of cancer. In some embodiments the cancer can be breast cancer (for example triple negative breast cancer), lung cancer (for example non-small cell lung cancer), pancreatic cancer, renal cancer, or hepatocellular cancer.

The compound of Formula (I) will normally be administered to a warm-blooded animal at a unit dose within the range 5-5000 mg/m$^2$ body area of the animal, i.e., approximately 0.1-100 mg/kg, and this normally provides a therapeutically-effective dose. A unit dose form such as a tablet or capsule will usually contain, for example 1-250 mg of active ingredient. The daily dose will necessarily be varied depending upon the host treated, the particular route of administration, any therapies being co-administered, and the severity of the illness being treated. Accordingly the practitioner who is treating any particular patient may determine the optimum dosage.

EXAMPLES

The various embodiments are illustrated by the following Examples. The invention is not to be interpreted as being limited to the Examples.

During the preparation of the Examples, generally:
a) Operations were carried out at ambient temperature, i.e. in the range of about 17 to 30° C. and under an atmosphere of an inert gas such as nitrogen unless otherwise stated;
b) Evaporations were carried out by rotary evaporation or utilising Genevac equipment in vacuo and work-up procedures were carried out after removal of residual solids by filtration;

c) Flash chromatography purifications were performed on an automated Isco Combiflash Companion using Grace Resolve prepacked silica columns, and (reverse phase flash) Isco Combiflash Rf using RediSep Gold C18 columns;
d) Yields, where present, are not necessarily the maximum attainable;
e) Structures of end-products of Formula (I) were confirmed by nuclear magnetic resonance (NMR) spectroscopy, with NMR chemical shift values measured on the delta scale. Proton magnetic resonance spectra were determined using a Bruker Avance 700 (700 MHz), Bruker Avance 500 (500 MHz), Bruker 400 (400 MHz) or Bruker 300 (300 MHz) instrument; $^{19}$F NMR were determined at 282 MHz or 376 MHz; $^{13}$C NMR were determined at 75 MHz or 100 MHz; measurements were taken at around 20-30° C. unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal;
f) End-products of Formula (I) were also characterised by mass spectroscopy following liquid chromatography (LCMS), using a HPLC system based on a Waters 2790/95 LC system with a 2996 PDA and a 2000 amu ZQ single quadrupole mass spectrometer. The solvents used were A=Water, B=Acetonitrile, C=50:50 acetonitrile:water 0.1% formic acid and D=50:50 acetonitrile:water 0.1% ammonium hydroxide. At a flow rate of 1.1 mL/min 5 µL of sample was injected onto a 50×2.1 5 µm Phenomenex Gemini NX column. The gradient ran from 95% A to 95% B for 4.0 mins with a constant 5% infusion of C (for acid analysis, D is used for base analysis). The flow was held at 95% B for 0.5 mins before returning to start conditions. The Data was acquired from 150 to 850 amu in both positive and negative mode on the Mass Spectrometer and 220-320 nm on the PDA. LCMS was also performed on a UPLC system utilising a Waters Acquity Binary pump with sample manager, Acquity PDA and an SQD Mass spectrometer. The solvents used were A1=0.1% formic acid (aq), B1 0.1% formic acid in acetonitrile, A2=0.1% ammonium hydroxide (aq) and B2 0.1% ammonium hydroxide in acetonitrile. At a flow rate of 1 mL/min 1 µL of sample was injected onto a 50×2.1 1.7 um Waters BEH column (at 40° C.). The gradient ran from 97% A1 to 97% B1 over 1.30 mins before being held for 0.2 min and returning to start conditions (substitute A1 and B1 for A2 and B2 for base analysis). Data was acquired from 150-1000 amu in positive and negative ion mode on the mass spectrometer and 245-320 amu on the PDA;
g) Intermediates were not generally fully characterised and purity was assessed by thin layer chromatographic, mass spectral, HPLC and/or NMR analysis;
h) The following abbreviations have been used: h=hour(s); r.t.=room temperature (~17-30° C.); conc.=concentrated; FCC=flash column chromatography using silica; AIBN=azobisisobutyronitrile; DCM=dichloromethane; DIPEA=di-isopropyl ethylamine; DMA=N,N-dimethylacetamide; DMF=N,N-dimethylformamide; DMSO=dimethylsulfoxide; EDC=1-Ethyl-3-(3-dimethylaminopropyl)carbodiimide; Et$_2$O=diethyl ether; EtOAc=ethyl acetate; EtOH=ethanol; HATU=1-[bis(dimethylamino)methylene]-1H-1,2,3-triazolo[4,5-b]pyridinium 3-oxid hexafluorophosphate; HOBT=hydroxybenzotriazole; K$_2$CO$_3$=potassium carbonate; MeOH=methanol; MeCN=acetonitrile; MgSO$_4$=anhydrous magnesium sulphate; Na$_2$SO$_4$=anhydrous sodium sulphate; NBS=N-bromo succinimide; TFA=trifluoroacetic acid; THF=tetrahydrofuran; sat.=saturated aqueous solution.

In a number of the examples below, a diastereomeric pair of compounds is described. For example, the compounds of Example 1(a) and Example 1(b) represent a diastereomeric pair of compounds, formed as a mixture in the product of a single reaction and subsequently separated. In such examples, any assignment of stereochemistry is not absolute. By way of illustration, Examples 1(a) and 1(b) relate to the (2S,3R) and (2R,3R) diastereomers of the named compound; however, it is not intended convey that Example 1(a) is definitively assigned as the (2S,3R) diastereomer and Example 1(b) as the (2R,3R) diastereomer.

Example 1(a) and 1(b)

(2S)-2-Methoxy-2-(3-methoxyphenyl)-N-[5-[[(3R)-1-(6-methylpyridazin-3-yl)pyrrolidin-3-yl]amino]-1,3,4-thiadiazol-2-yl]acetamide and (2R)-2-Methoxy-2-(3-methoxyphenyl)-N-[5-[[(3R)-1-(6-methylpyridazin-3-yl)pyrrolidin-3-yl]amino]-1,3,4-thiadiazol-2-yl]acetamide

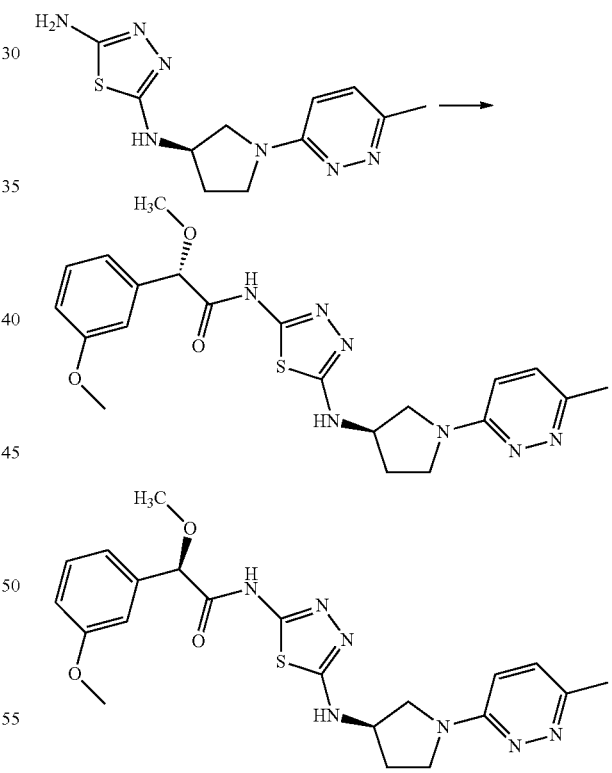

HATU (329 mg, 0.87 mmol) was added to 2-methoxy-2-(3-methoxyphenyl)acetic acid (Intermediate 14, 141 mg, 0.72 mmol), N2-[(3R)-1-(6-methylpyridazin-3-yl)pyrrolidin-3-yl]-1,3,4-thiadiazole-2,5-diamine (Intermediate 1, 200 mg, 0.72 mmol) and DIPEA (0.25 mL, 1.44 mmol) in DMF (6 mL) at 21° C. under nitrogen. The resulting solution was stirred at 21° C. for 2 hours. The crude mixture was purified by ion exchange chromatography, using an SCX column. The desired product was eluted from the column using 1M NH₃ in MeOH and pure fractions were evaporated to dryness to afford crude product which was further purified by FCC (SiO₂, 0 to 12% MeOH in DCM). Pure fractions were evaporated to dryness to afford the mixture of diastereoisomers as a pale yellow gum (95 mg). The diastereoisomers were separated by preparative HPLC (Lux C2 column, 20 μm, 50 mm×250 mm, 100% MeOH at 200 mL/min) to give:

First eluted isomer example 1(a) 2-methoxy-2-(3-methoxyphenyl)-N-[5-[[(3R)-1-(6-methylpyridazin-3-yl)pyrrolidin-3-yl]amino]-1,3,4-thiadiazol-2-yl]acetamide (58 mg, 18%). ¹H NMR (400 MHz, DMSO-d6, 30° C.) δ 2.05 (1H, td), 2.21-2.35 (1H, m), 2.41 (3H, s), 3.40-3.47 (1H, m), 3.55 (2H, ddd), 3.69-3.75 (4H, m), 4.31-4.46 (1H, m), 4.93 (1H, s), 6.82 (1H, d), 6.87-6.94 (1H, m), 6.99-7.07 (2H, m), 7.22 (1H, d), 7.29 (1H, t), 7.61 (1H, d), 12.13 (1H, s). m/z: ES⁺ [M+H]⁺ 456.

Second eluted isomer example 1(b) 2-methoxy-2-(3-methoxyphenyl)-N-[5-[[(3R)-1-(6-methylpyridazin-3-yl)pyrrolidin-3-yl]amino]-1,3,4-thiadiazol-2-yl]acetamide (55 mg, 17%). ¹H NMR (400 MHz, DMSO-d6, 30° C.) δ 2.05 (1H, td), 2.21-2.35 (1H, m), 2.41 (3H, s), 3.4-3.47 (1H, m), 3.55 (2H, ddd), 3.69-3.75 (4H, m), 4.31-4.46 (1H, m), 4.93 (1H, s), 6.82 (1H, d), 6.87-6.94 (1H, m), 6.99-7.07 (2H, m), 7.22 (1H, d), 7.29 (1H, t), 7.61 (1H, d), 12.13 (1H, s). m/z: ES⁺ [M+H]⁺ 456.

Example 2

(2S)-N-[5-[[(3R)-1-(6-Fluoropyridazin-3-yl)pyrrolidin-3-yl]amino]-1,3,4-thiadiazol-2-yl]-2-methoxy-2-phenyl-acetamide

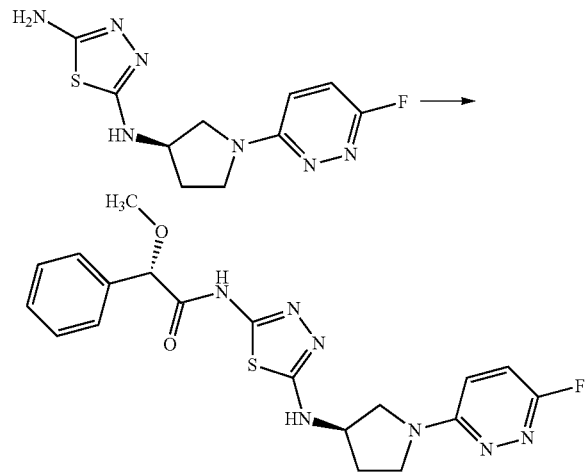

HOBT (120 mg, 0.78 mmol) was added to N2-[(3R)-1-(6-fluoropyridazin-3-yl)pyrrolidin-3-yl]-1,3,4-thiadiazole-2,5-diamine (Intermediate 4, 220 mg, 0.78 mmol), (2S)-2-methoxy-2-phenyl-acetic acid (130 mg, 0.78 mmol) and EDC (300 mg, 1.56 mmol) in DMF (3 mL) at 25° C. The resulting mixture was stirred at 25° C. for 3 hours. The crude product was purified by preparative HPLC (XBridge C18 OBD column, 5 μm, 50 mm×150 mm). Decreasingly polar mixtures of water (containing 0.05% formic acid) and MeCN were used as a mobile phase. Fractions containing the desired compound were evaporated to dryness to afford example 2 (2S)-N-[5-[[(3R)-1-(6-fluoropyridazin-3-yl)pyrrolidin-3-yl]amino]-1,3,4-thiadiazol-2-yl]-2-methoxy-2-phenyl-acetamide (95 mg, 27.8%) as a white solid. ¹H NMR (400 MHz, MeOD, 22° C.) δ 2.16-2.23 (m, 1H), 2.36-2.44 (m, 1H), 3.44 (s, 3H), 3.55-3.69 (m, 3H), 3.82-3.86 (m, 1H), 4.46-4.51 (m, 1H), 4.93 (s, 1H), 7.15-7.19 (m, 1H), 7.24-7.27 (m, 1H), 7.35-7.43 (m, 3H), 7.47-7.49 (m, 2H). m/z: ES⁺ [M+H]⁺ 430.

Example 3

(2S)-N-[5-[[(3R)-1-(6-Fluoropyridazin-3-yl)pyrrolidin-3-yl]amino]-1,3,4-thiadiazol-2-yl]-2-methoxy-2-(3-methoxyphenyl)acetamide

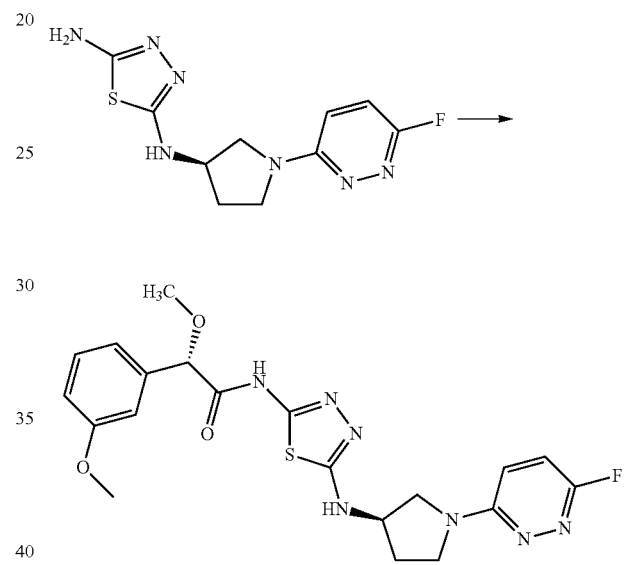

HATU (405 mg, 1.07 mmol) was added to (2S)-2-methoxy-2-(3-methoxyphenyl)acetic acid (Intermediate 12, 174 mg, 0.89 mmol), N2-[(3R)-1-(6-fluoropyridazin-3-yl)pyrrolidin-3-yl]-1,3,4-thiadiazole-2,5-diamine (Intermediate 4, 250 mg, 0.89 mmol) and DIPEA (0.155 mL, 0.89 mmol) in DMF (8 mL) at 21° C. under N₂. The resulting solution was stirred at 0° C. for 45 minutes. The crude product was purified by ion exchange chromatography, using an SCX column. The desired product was eluted from the column using 1M NH₃ in MeOH and pure fractions were evaporated to dryness to afford a gum. The crude product was purified by FCC (SiO₂, 0 to 9% MeOH in DCM). Pure fractions were evaporated to dryness, triturated with ether/DCM and filtered to afford example 3 (2S)-N-[5-[[(3R)-1-(6-fluoropyridazin-3-yl)pyrrolidin-3-yl]amino]-1,3,4-thiadiazol-2-yl]-2-methoxy-2-(3-methoxyphenyl)acetamide (185 mg, 45%) as a cream solid. ¹H NMR (400 MHz, DMSO-d6, 30° C.) δ 2.12 (1H, td), 2.3-2.46 (1H, m), 3.37 (3H, s), 3.52 (1H, dd), 3.59-3.67 (2H, m), 3.81 (4H, m), 4.34-4.56 (1H, m), 5.00 (1H, s), 6.97 (1H, ddd), 7.03-7.14 (2H, m), 7.22 (1H, dd), 7.32-7.51 (2H, m), 7.73 (1H, d), 12.20 (1H, s). m/z: ES⁺ [M+H]⁺ 486.

Example 4(a) and 4(b)

(2S)-2-Ethoxy-2-(3-methoxyphenyl)-N-[5-[[(3R)-1-(6-methylpyridazin-3-yl)pyrrolidin-3-yl]amino]-1,3,4-thiadiazol-2-yl]acetamide and (2R)-2-Ethoxy-2-(3-methoxyphenyl)-N-[5-[[(3R)-1-(6-methylpyridazin-3-yl)pyrrolidin-3-yl]amino]-1,3,4-thiadiazol-2-yl]acetamide

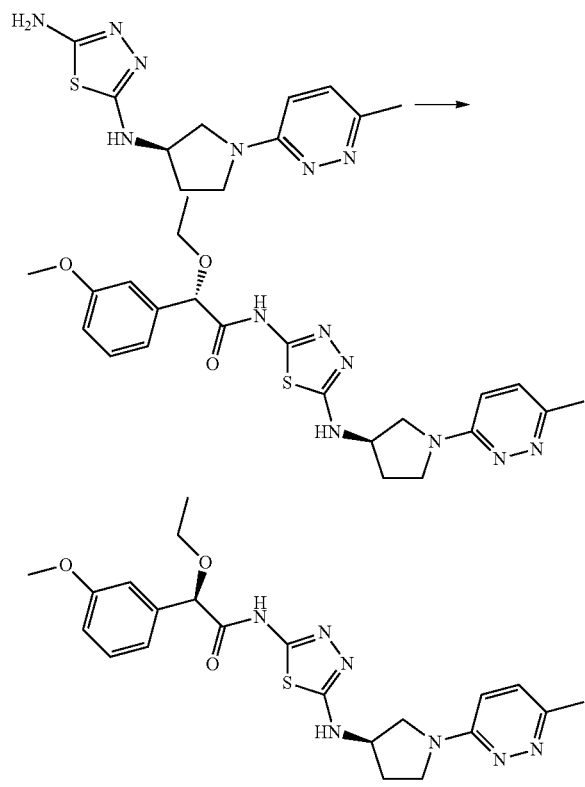

2-Ethoxy-2-(3-methoxyphenyl)acetic acid (Intermediate 15, 0.11 g, 0.54 mmol) and N2-[(3R)-1-(6-methylpyridazin-3-yl)pyrrolidin-3-yl]-1,3,4-thiadiazole-2,5-diamine (Intermediate 1, 0.15 g, 0.54 mmol) were weighed into a round a bottom flask followed by DIPEA (0.1 mL, 0.54 mmol) and DMF (5 mL). The resultant solution was then treated with HATU (0.21 g, 0.54 mmol) and allowed to stir at r.t. under $N_2$ for 24 hours. The solvent was removed under reduced pressure and the residual gum was dissolved in DCM, adsorbed onto silica and purified by FCC ($SiO_2$ 0-10% MeOH in DCM). Evaporation of the pure fractions under reduced pressure yielded the title compound as a light yellow foam. The foam was dissolved in methanol and added to an SCX ion exchange column which was washed with DCM, then methanol and then eluted with 2M $NH_3$ in MeOH. The solvent was removed under reduced pressure and further purified by preparative HPLC (SunFire C18 column, 5 μm, 50 mm×19 mm, flow rate 25 mL/min). Decreasingly polar ratios of water and MeCN containing 0.1% formic acid were used as a mobile phase. Pure fractions were evaporated to dryness to afford the product as a mixture of diastereoisomers as a white solid (67 mg). The diastereoisomers were separated by preparative HPLC (Phenomenex Lux C4 column, 20 μm, 50 mm×250 mm, MeOH at 120 mL/min) to give:

First eluted isomer example 4(a) 2-ethoxy-2-(3-methoxyphenyl)-N-[5-[[(3R)-1-(6-methylpyridazin-3-yl)pyrrolidin-3-yl]amino]-1,3,4-thiadiazol-2-yl]acetamide (25 mg, 37%). $^1$H NMR (400 MHz, DMSO-d6, 30° C.) δ 1.17 (3H, t), 1.99-2.09 (1H, m), 2.22-2.32 (1H, m), 2.40 (3H, s), 3.40-3.56 (5H, m), 3.69-3.73 (1H, m), 3.74 (3H, s), 4.32-4.40 (1H, m), 5.04 (1H, s), 6.83 (1H, d), 6.89 (1H, dd), 7.00-7.05 (2H, m), 7.22 (1H, d), 7.28 (1H, t), 7.65 (1H, d), 12.10 (1H, s). m/z: ES$^+$ [M+H]$^+$ 470.

Second eluted isomer example 4(b) 2-ethoxy-2-(3-methoxyphenyl)-N-[5-[[(3R)-1-(6-methylpyridazin-3-yl)pyrrolidin-3-yl]amino]-1,3,4-thiadiazol-2-yl]acetamide (25 mg, 37%). $^1$H NMR (400 MHz, DMSO-d6, 30° C.) δ 1.17 (3H, t), 1.97-2.09 (1H, m), 2.21-2.31 (1H, m), 2.40 (3H, s), 3.39-3.56 (5H, m), 3.70-3.73 (1H, m), 3.74 (3H, s), 4.33-4.40 (1H, m), 5.04 (1H, s), 6.84 (1H, d), 6.87-6.92 (1H, m), 7.01-7.05 (2H, m), 7.23 (1H, d), 7.28 (1H, t), 7.65 (1H, d), 12.11 (1H, s). m/z: ES$^+$ [M+H]$^+$ 470.

Example 5(a) and 5(b)

(2S)-2-(4-Fluorophenyl)-2-methoxy-N-[5-[[(3R)-1-(6-methylpyridazin-3-yl)pyrrolidin-3-yl]amino]-1,3,4-thiadiazol-2-yl]acetamide and (2R)-2-(4-Fluorophenyl)-2-methoxy-N-[5-[[(3R)-1-(6-methylpyridazin-3-yl)pyrrolidin-3-yl]amino]-1,3,4-thiadiazol-2-yl]acetamide

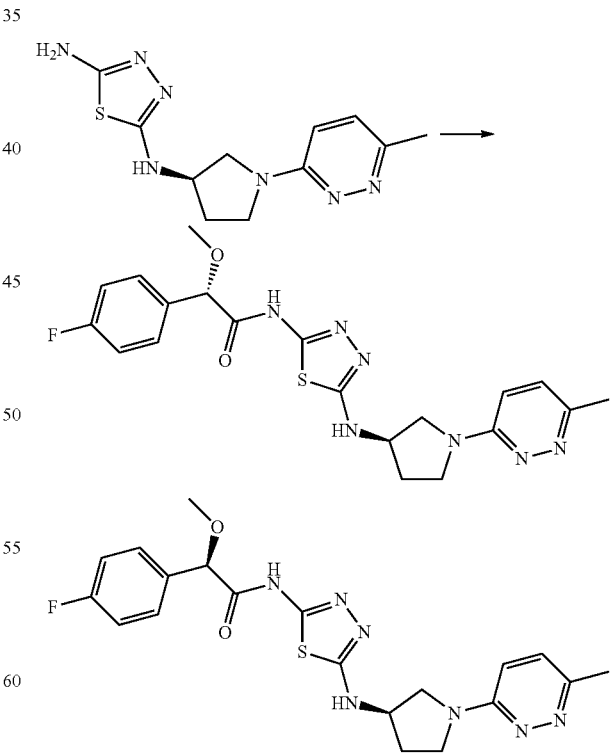

N2-[(3R)-1-(6-Methylpyridazin-3-yl)pyrrolidin-3-yl]-1,3,4-thiadiazole-2,5-diamine (Intermediate 1, 0.15 g, 0.541 mmol) and 2-(4-fluorophenyl)-2-methoxyacetic acid (Intermediate 16, 0.1 g, 0.541 mmol) were dissolved in DMF (2 mL) at r.t under $N_2$. The mixture was stirred for 5 min before addition of DIPEA (0.34 mL, 1.943 mmol) and HATU (0.21 g, 0.541 mmol), then at r.t. for 2 h. The crude mixture was then passed through a 5 g SCX column washed with MeOH then eluted with 2N $NH_3$ in MeOH. The basic fraction was evaporated under reduced pressure to give an orange gum which was purified by preparative HPLC (SunFire C18 column, 5 μm, 50 mm×19 mm, flow rate 25 mL/min). Decreasingly polar ratios of water and MeCN containing 0.1% formic acid were used as a mobile phase. Pure fractions were combined, evaporated under reduced pressure and passed through a 2 g SCX column washed with MeOH then eluted with 2N $NH_3$ in MeOH. The basic fraction was evaporated to dryness to afford the mixture of diastereoisomers as an off-white foam. The diastereoisomers were separated by preparative HPLC (Amy-C column, 5 μm, 20 mm×250 mm, 2:3 heptane:EtOH containing 0.1% v/v $NH_3$ modifier at 21 mL/min) to give:

First eluted isomer example 5(a) 2-(4-fluorophenyl)-2-methoxy-N-[5-[[(3R)-1-(6-methylpyridazin-3-yl)pyrrolidin-3-yl]amino]-1,3,4-thiadiazol-2-yl]acetamide (55.3 mg, 23.0%). $^1$H NMR (400 MHz, DMSO-d6, 21° C.) δ 2.04 (1H, dq), 2.26 (1H, dt), 2.41 (3H, s), 3.30 (3H, s), 3.57-3.41 (3H, m), 3.72 (1H, dd), 4.36 (1H, q), 4.98 (1H, s), 6.83 (1H, d), 7.22 (3H, ddd), 7.55-7.44 (2H, m), 7.66 (1H, d), 12.28 (s, 1H). m/z: ES$^+$ [M+H]$^+$ 444.

Second eluted isomer example 5(b) 2-(4-fluorophenyl)-2-methoxy-N-[5-[[(3R)-1-(6-methylpyridazin-3-yl)pyrrolidin-3-yl]amino]-1,3,4-thiadiazol-2-yl]acetamide (59.2 mg, 24.7%). $^1$H NMR (400 MHz, DMSO-d6, 21° C.) δ 2.04 (1H, dq), 2.31-2.23 (1H, m), 2.41 (3H, s), 3.30 (3H, s), 3.44 (1H, dd), 3.59-3.49 (2H, m), 3.71 (1H, dd), 4.36 (1H, q), 4.97 (1H, s), 6.82 (1H, d), 7.22 (3H, ddd), 7.53-7.46 (2H, m), 7.64 (1H, d), 12.28 (1H, s). m/z: ES$^+$ [M+H]$^+$ 444.

Example 6(a) and 6(b)

(2S)-2-(4-Fluoro-3-methoxy-phenyl)-2-methoxy-N-[5-[[(3R)-1-(6-methylpyridazin-3-yl)pyrrolidin-3-yl]amino]-1,3,4-thiadiazol-2-yl]acetamide and (2R)-2-(4-Fluoro-3-methoxy-phenyl)-2-methoxy-N-[5-[[(3R)-1-(6-methylpyridazin-3-yl)pyrrolidin-3-yl]amino]-1,3,4-thiadiazol-2-yl]acetamide

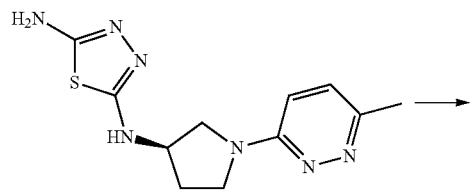

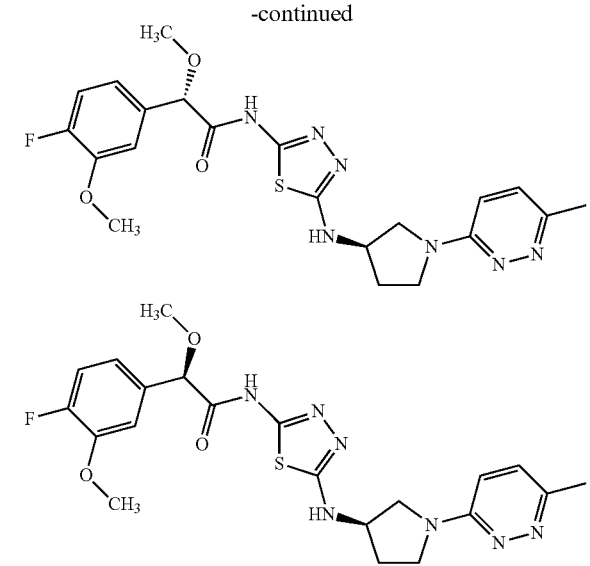

N2-[(3R)-1-(6-Methylpyridazin-3-yl)pyrrolidin-3-yl]-1,3,4-thiadiazole-2,5-diamine (Intermediate 1, 200 mg, 0.72 mmol) and 2-(4-fluoro-3-methoxy-phenyl)-2-methoxy-acetic acid (Intermediate 18, 150 mg, 0.72 mmol) were dissolved in DMF (2 mL) at r.t under nitrogen. The mixture was stirred for 5 mins before addition of DIPEA (0.34 mL, 1.94 mmol) and HATU (0.27 g, 0.72 mmol) then stirred at r.t. overnight. The crude mixture was passed through a 5 g SCX column washed with MeOH then eluted with 2 M $NH_3$ in MeOH. The basic fraction was evaporated to give crude product as an orange gum which was purified by preparative HPLC (SunFire C18 column, 5 μm, 50 mm×19 mm, flow rate 25 mL/min). Decreasingly polar ratios of water and MeCN containing 0.1% formic acid were used as a mobile phase. Pure fractions were combined, evaporated and passed through a 2 g SCX column washed with MeOH then eluted with 2M $NH_3$ in MeOH. The basic fraction was evaporated to give the mixture of diastereoisomers as an off-white solid. The diastereoisomers were then separated by SFC (Lux C3 column, 5 μm, 21.2 mm×250 mm, MeOH/$CO_2$ 35% containing $NH_3$ modifier, 50 mL/min) to give:

First eluted isomer example 6(a) 2-(4-fluoro-3-methoxy-phenyl)-2-methoxy-N-[5-[[(3R)-1-(6-methylpyridazin-3-yl)pyrrolidin-3-yl]amino]-1,3,4-thiadiazol-2-yl]acetamide (34 mg, 10%). $^1$H NMR (400 MHz, DMSO-d6, 21° C.) δ 1.98-2.12 (1H, m), 2.21-2.33 (1H, m), 2.41 (3H, s), 3.32 (3H, s), 3.40-3.58 (3H, m), 3.69-3.79 (1H, m), 3.84 (3H, s), 4.32-4.41 (1H, m), 4.95 (s, 1H), 6.83 (1H, d), 6.98-7.05 (1H, m), 7.19-7.28 (3H, m), 7.68 (1H, d). m/z: ES$^+$[M+H]$^+$ 474.

Second eluted isomer example 6(b) 2-(4-fluoro-3-methoxy-phenyl)-2-methoxy-N-[5-[[(3R)-1-(6-methylpyridazin-3-yl)pyrrolidin-3-yl]amino]-1,3,4-thiadiazol-2-yl]acetamide (44 mg, 13%). $^1$H NMR (400 MHz, DMSO-d6, 21° C.) δ 1.99-2.10 (1H, m), 2.23-2.34 (1H, m), 2.41 (3H, s), 3.31 (3H, s), 3.41-3.48 (1H, m), 3.50-3.56 (2H, m), 3.67-3.78 (1H, m), 3.84 (3H, s), 4.32-4.39 (1H, m), 4.94 (1H, s), 6.82 (1H, d), 6.98-7.04 (1H, m), 7.17-7.30 (3H, m), 7.65 (1H, d). m/z: ES$^+$[M+H]$^+$ 474.

Example 7(a) and 7(b)

(2S)-2-Methoxy-N-[5-[[(3R)-1-(6-methylpyridazin-3-yl)pyrrolidin-3-yl]amino]-1,3,4-thiadiazol-2-yl]-2-[3-(trifluoromethoxy)phenyl]acetamide and (2R)-2-Methoxy-N-[5-[[(3R)-1-(6-methylpyridazin-3-yl)pyrrolidin-3-yl]amino]-1,3,4-thiadiazol-2-yl]-2-[3-(trifluoromethoxy)phenyl]acetamide

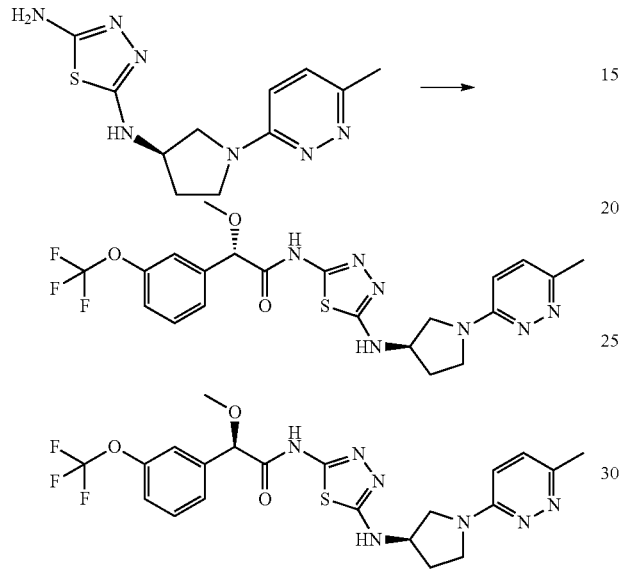

DIPEA (0.14 mL, 0.81 mmol), HATU (247 mg, 0.65 mmol) and 2-methoxy-2-[3-(trifluoromethoxy)phenyl]acetic acid (Intermediate 19, 160 mg, 0.65 mmol) were added to a solution of N2-[(3R)-1-(6-methylpyridazin-3-yl)pyrrolidin-3-yl]-1,3,4-thiadiazole-2,5-diamine (Intermediate 1, 150 mg, 0.54 mmol) in DMF (4 mL). The mixture was stirred at r.t. for 18 h. This was then diluted with water (5 mL) and then extracted into DCM (10 mL), evaporated and purified by preparative HPLC (XBridge OBD C18 column, 5 μm, 50 mm×19 mm, flow rate was 25 mL/min). Decreasingly polar ratios of water and MeCN containing 0.3 mL/L NH$_4$OH were used as a mobile phase. Pure fractions were then evaporated to give a mixture of diastereoisomers. The diastereoisomers were separated by preparative HPLC (Amy-C column, 5 μm, 4.6 mm×250 mm, heptane/EtOH 7/3 containing NH$_3$ modifier, 21 mL/min) to give:

First eluted isomer example 7(a) 2-methoxy-N-[5-[[(3R)-1-(6-methylpyridazin-3-yl)pyrrolidin-3-yl]amino]-1,3,4-thiadiazol-2-yl]-2-[3-(trifluoromethoxy)phenyl]acetamide (50 mg, 18%). $^1$H NMR (400 MHz, DMSO-d6, 21° C.) δ 1.96-2.11 (1H, m), 2.20-2.37 (1H, m), 2.41 (3H, s), 3.34 (3H, s), 3.42-3.60 (3H, m), 3.66-3.78 (1H, m), 4.37 (1H, q), 5.07 (1H, s), 6.84 (1H, d), 7.23 (1H, d), 7.37 (1H, d), 7.41-7.58 (3H, m), 7.72 (1H, d), 12.37 (1H, s). m/z: ES$^+$ [M+H]$^+$ 510.

Second eluted isomer example 7(b) 2-methoxy-N-[5-[[(3R)-1-(6-methylpyridazin-3-yl)pyrrolidin-3-yl]amino]-1,3,4-thiadiazol-2-yl]-2-[3-(trifluoromethoxy)phenyl]acetamide (34 mg, 12%). $^1$H NMR (400 MHz, DMSO-d6, 21° C.) δ 1.97-2.13 (1H, m), 2.20-2.34 (1H, m), 2.41 (3H, s), 3.34 (3H, s), 3.39-3.60 (3H, m), 3.66-3.77 (1H, m), 4.36 (1H, d), 5.07 (1H, s), 6.83 (1H, d), 7.23 (1H, d), 7.37 (1H, d), 7.43-7.60 (3H, m), 7.72 (1H, d), 12.36 (1H, s). m/z: ES$^+$[M+H]$^+$ 510.

Examples 8(a) and 8(b)

(2S)-[3-(Difluoromethoxy)phenyl]-2-methoxy-N-[5-[[(3R)-1-(6-methylpyridazin-3-yl)pyrrolidin-3-yl]amino]-1,3,4-thiadiazol-2-yl]acetamide and (2R)-[3-(Difluoromethoxy)phenyl]-2-methoxy-N-[5-[[(3R)-1-(6-methylpyridazin-3-yl)pyrrolidin-3-yl]amino]-1,3,4-thiadiazol-2-yl]acetamide

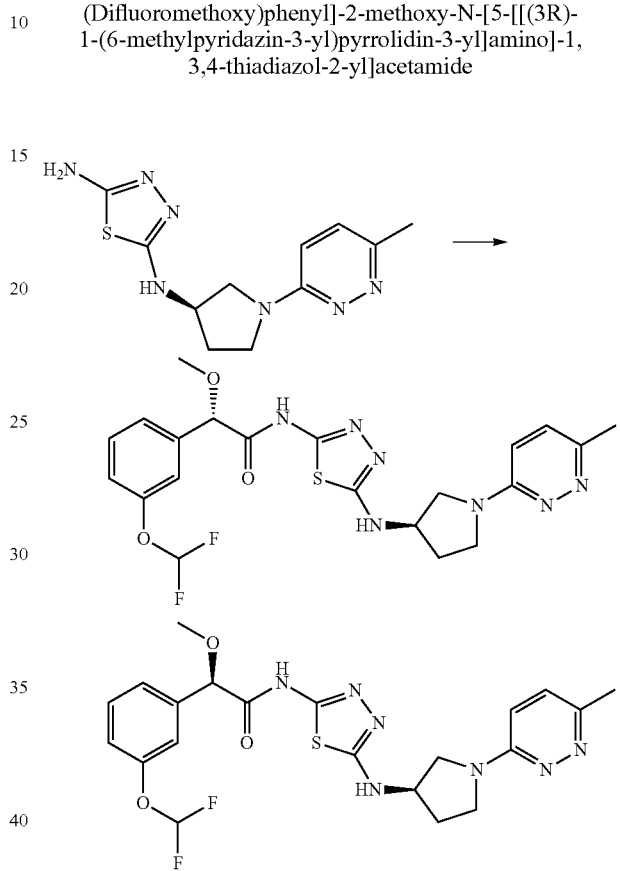

2-[3-(Difluoromethoxy)phenyl]-2-methoxy-acetic acid (Intermediate 20, 0.11 g, 0.469 mmol) and N2-[(3R)-1-(6-methylpyridazin-3-yl)pyrrolidin-3-yl]-1,3,4-thiadiazole-2,5-diamine (Intermediate 1, 0.13 g, 0.469 mmol) were weighed into a round bottomed flask. DMF (3 mL) and DIPEA (0.15 g, 1.172 mmol) were added followed by HATU (0.18 g, 0.469 mmol) and the resultant solution was allowed to stir at r. t. under nitrogen for 15 h. The solvent was removed under reduced pressure and the residual gum was dissolved in DCM, absorbed onto silica and purified by FCC (SiO$_2$, 1-10% MeOH containing 0.1% NH$_3$ in DCM). Evaporation of the pure fractions under reduced pressure gave a pale yellow gum that was separated by preparative chiral SFC (Lux C3 column, 5 μm, 21.2 mm×250 mm, flow rate 50 mL/min at a wavelength of 210 nm with 40:60 MeOH:CO$_2$+0.1% NH$_3$ as eluent) to give:

First eluted isomer example 8(a) [3-(difluoromethoxy)phenyl]-2-methoxy-N-[5-[[(3R)-1-(6-methylpyridazin-3-yl)pyrrolidin-3-yl]amino]-1,3,4-thiadiazol-2-yl]acetamide (48 mg, 20%). $^1$H NMR (400 MHz, DMSO-d6, 30° C.) δ 2.07-2.00 (1H, m), 2.31-2.22 (1H, m), 2.40 (3H, s), 3.34 (3H, s), 3.58-3.41 (3H, m), 3.71 (1H, dd), 4.38-4.34 (1H, m), 5.01 (1H, s), 6.83 (1H, d), 7.49-7.04 (6H, m), 7.71 (1H, d), 12.31 (1H, s). m/z: ES$^+$ [M+H]$^+$ 492.

Second eluted isomer example 8(b) [3-(difluoromethoxy)phenyl]-2-methoxy-N-[5-[[(3R)-1-(6-methylpyridazin-3-yl)pyrrolidin-3-yl]amino]-1,3,4-thiadiazol-2-yl]acetamide (45 mg, 19%). ¹H NMR (400 MHz, DMSO-d6, 30° C.) δ 2.08-2.00 (1H, m), 2.34-2.21 (1H, m), 2.40 (3H, s), 3.32 (3H, s), 3.57-3.42 (3H, m), 3.71 (1H, dd), 4.36 (1H, m), 5.01 (1H, s), 6.82 (1H, d), 7.49-7.04 (6H, m), 7.69 (1H, d), 12.26 (1H, s). m/z: ES⁺ [M+H]⁺ 492.

Example 9(a) and 9(b)

(2S)-2-[3-(difluoromethoxy)phenyl]-N-[5-[[(3R)-1-(6-fluoropyridazin-3-yl)pyrrolidin-3-yl]amino]-1,3,4-thiadiazol-2-yl]-2-methoxy-acetamide and (2R)-2-[3-(difluoromethoxy)phenyl]-N-[5-[[(3R)-1-(6-fluoropyridazin-3-yl)pyrrolidin-3-yl]amino]-1,3,4-thiadiazol-2-yl]-2-methoxy-acetamide

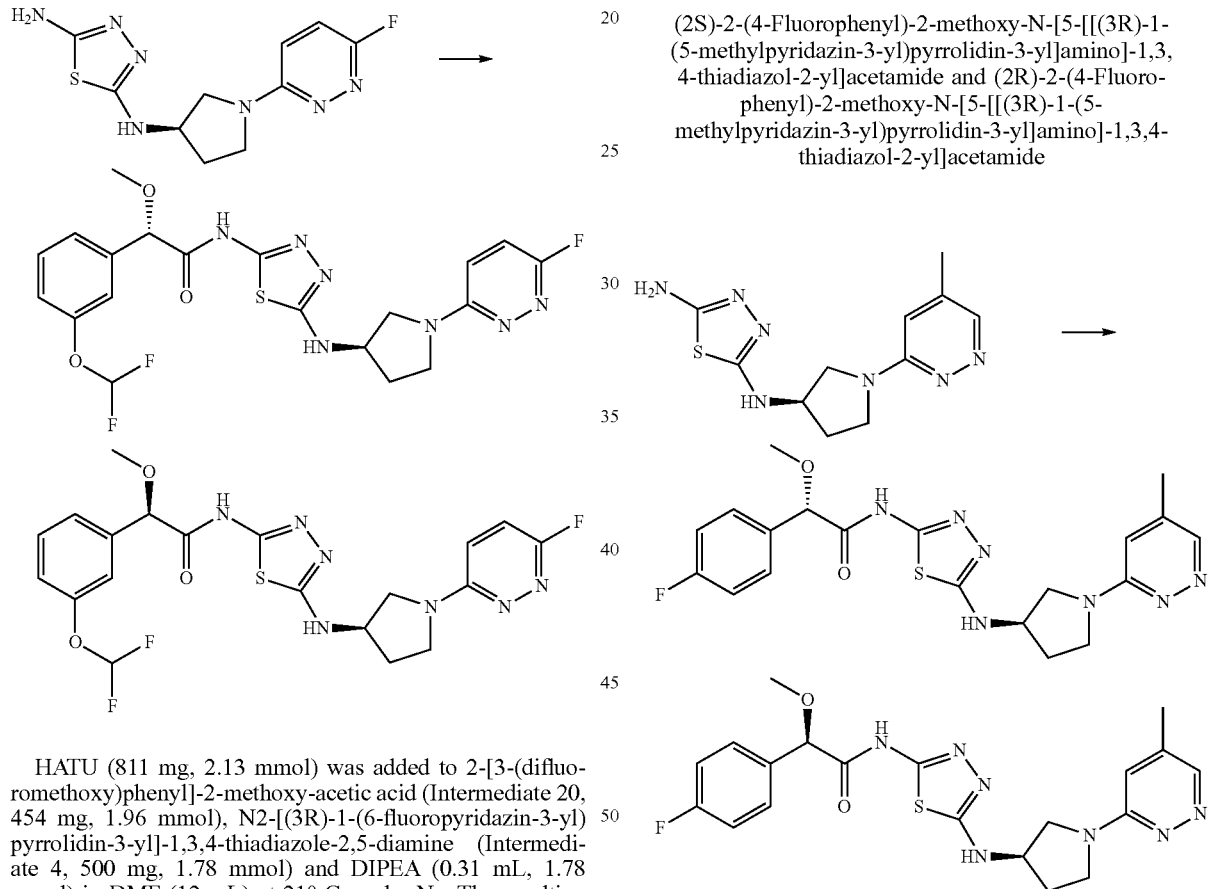

HATU (811 mg, 2.13 mmol) was added to 2-[3-(difluoromethoxy)phenyl]-2-methoxy-acetic acid (Intermediate 20, 454 mg, 1.96 mmol), N2-[(3R)-1-(6-fluoropyridazin-3-yl)pyrrolidin-3-yl]-1,3,4-thiadiazole-2,5-diamine (Intermediate 4, 500 mg, 1.78 mmol) and DIPEA (0.31 mL, 1.78 mmol) in DMF (12 mL) at 21° C. under N₂. The resulting solution was stirred at 21° C. for 45 minutes. The crude product was purified by ion exchange chromatography, using an SCX column. The desired product was eluted from the column using 1M NH₃ in MeOH and the fractions were evaporated to a gum. The crude product was purified by FCC (SiO₂, 0-8% MeOH in DCM). The fractions were evaporated to dryness to give a gummy solid. The crude product was further purified by FCC (SiO₂, 0-9% MeOH in EtOAc). Pure fractions were evaporated to dryness, triturated with DCM/ether and filtered to afford the mixture of diastereoisomers as a yellow solid (210 mg). The diastereoisomers were separated by preparative HPLC (Phenomenex Lux C2 column, 20 μm, 50 mm×250 mm using EtOH as eluent at 120 mL/min) to give:

First eluted isomer example 9(a) (2S)-2-[3-(difluoromethoxy)phenyl]-N-[5-[[(3R)-1-(6-fluoropyridazin-3-yl)pyrrolidin-3-yl]amino]-1,3,4-thiadiazol-2-yl]-2-methoxy-acetamide (72 mg, 8%). ¹H NMR (400 MHz, DMSO, 30° C.) δ 2.02 (1H, dd), 2.25 (1H, dq), 3.29 (3H, s), 3.39-3.57 (3H, m), 3.70 (1H, dd), 4.34 (1H, d), 4.98 (1H, s), 6.97-7.25 (3H, m), 7.27-7.35 (2H, m), 7.38-7.48 (1H, m), 7.64 (1H, d), 12.19 (1H, s). m/z: ES⁻ [M−H]⁻ 494.

Second eluted isomer example 9(b) (2R)-2-[3-(difluoromethoxy)phenyl]-N-[5-[[(3R)-1-(6-fluoropyridazin-3-yl)pyrrolidin-3-yl]amino]-1,3,4-thiadiazol-2-yl]-2-methoxy-acetamide (95 mg, 11%). ¹H NMR (400 MHz, DMSO, 30° C.) δ 2.02 (1H, dd), 2.25 (1H, dq), 3.29 (3H, s), 3.39-3.57 (3H, m), 3.70 (1H, dd), 4.34 (1H, d), 4.98 (1H, s), 6.97-7.25 (3H, m), 7.27-7.35 (2H, m), 7.38-7.48 (1H, m), 7.64 (1H, d), 12.19 (1H, s). m/z: ES⁻ [M−H]⁻ 494.

Example 10(a) and 10(b)

(2S)-2-(4-Fluorophenyl)-2-methoxy-N-[5-[[(3R)-1-(5-methylpyridazin-3-yl)pyrrolidin-3-yl]amino]-1,3,4-thiadiazol-2-yl]acetamide and (2R)-2-(4-Fluorophenyl)-2-methoxy-N-[5-[[(3R)-1-(5-methylpyridazin-3-yl)pyrrolidin-3-yl]amino]-1,3,4-thiadiazol-2-yl]acetamide

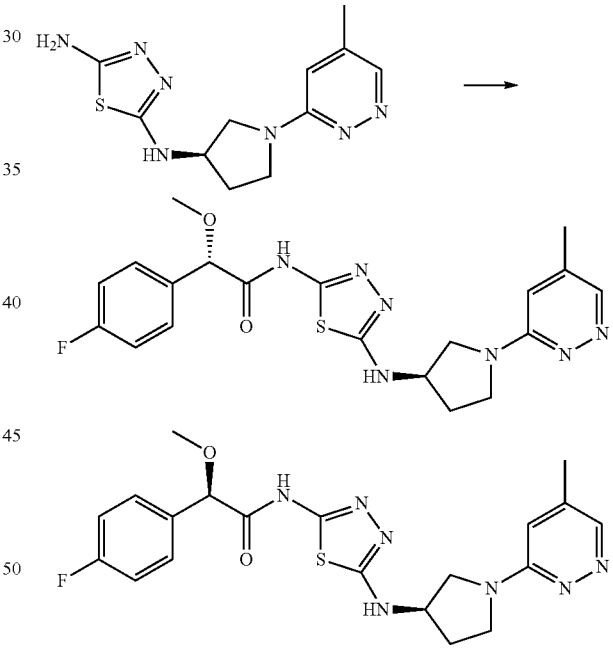

N2-[(3R)-1-(5-Methylpyridazin-3-yl)pyrrolidin-3-yl]-1,3,4-thiadiazole-2,5-diamine (Intermediate 7, 100 mg, 0.36 mmol) and 2-(4-fluorophenyl)-2-methoxyacetic acid (Intermediate 16, 66 mg, 0.36 mmol) were dissolved in DMF (2.0 mL) at r.t under N₂. The mixture was stirred for 5 minutes before addition of DIPEA (0.09 mL, 0.54 mmol) and HATU (165 mg, 0.43 mmol) then at r.t. overnight. The crude mixture was passed through a 5 g SCX column, washed with MeOH, then eluted with 2M NH₃ in MeOH. The basic fraction was evaporated to give an orange gum. The crude product was purified by preparative HPLC (SunFire C18 column, 5 μm, 50 mm×19 mm at 25 mL/min). Decreasingly polar ratios of water and MeCN containing 0.1% formic acid were used as a mobile phase. Fractions containing the desired mass were combined, evaporated and passed through a 5 g SCX column washed with MeOH then eluted with 2M NH₃ in MeOH. The basic fraction was evaporated to give the mixture of diastereoisomers as an off-white solid (70 mg). The diastereoisomers were separated by preparative HPLC (Lux C4 column, 20 μm, 50 mm×250 mm, 100% MeOH at 120 mL/min) to give:

First eluted isomer example 10(a) 2-(4-fluorophenyl)-2-methoxy-N-[5-[[(3R)-1-(5-methylpyridazin-3-yl)pyrrolidin-3-yl]amino]-1,3,4-thiadiazol-2-yl]acetamide (25 mg, 16%). ¹H NMR (400 MHz, DMSO, 30° C.) 2.01-2.11 (1H, m), 2.20 (3H, s), 2.28 (1H, dt), 3.31 (3H, s), 3.48 (1H, dd), 3.52-3.61 (2H, m), 3.74 (1H, dd), 4.33-4.41 (1H, m), 4.98 (1H, s), 6.69 (1H, s), 7.21 (2H, t), 7.47-7.53 (2H, m), 7.63 (1H, d), 8.36 (1H, s), 12.20 (1H, s). m/z: ES⁺ [M+H]⁺ 444.

Second eluted isomer example 10(b) 2-(4-fluorophenyl)-2-methoxy-N-[5-[[(3R)-1-(5-methylpyridazin-3-yl)pyrrolidin-3-yl]amino]-1,3,4-thiadiazol-2-yl]acetamide (26 mg, 17%). ¹H NMR (400 MHz, DMSO, 30° C.) 2.00-2.1 (1H, m), 2.21 (3H, s), 2.27 (1H, dt), 3.31 (3H, s), 3.45-3.60 (3H, m), 3.74 (1H, dd), 4.32-4.40 (1H, m), 4.97 (1H, s), 6.69 (1H, d), 7.17-7.25 (2H, m), 7.47-7.53 (2H, m), 7.59 (1H, d), 8.36 (1H, d). m/z: ES⁺ [M+H]⁺ 444.

Example 11(a) and 11(b)

(2S)-N-[5-[[(3R)-1-(5-chloropyridazin-3-yl)pyrrolidin-3-yl]amino]-1,3,4-thiadiazol-2-yl]-2-methoxy-2-(4-methoxyphenyl)acetamide and (2R)-N-[5-[[(3R)-1-(5-chloropyridazin-3-yl)pyrrolidin-3-yl]amino]-1,3,4-thiadiazol-2-yl]-2-methoxy-2-(4-methoxyphenyl)acetamide

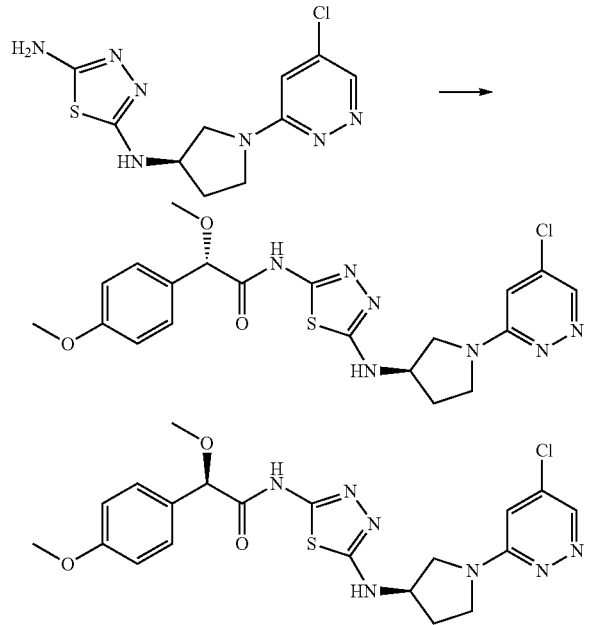

N2-[(3R)-1-(5-Chloropyridazin-3-yl)pyrrolidin-3-yl]-1,3,4-thiadiazole-2,5-diamine (Intermediate 9, 100 mg, 0.34 mmol) and 2-methoxy-2-(4-methoxyphenyl)acetic acid (Intermediate 21, 70 mg, 0.34 mmol) were dissolved in DMF (2.0 mL) and treated with DIPEA (0.15 mL, 0.84 mmol) and HATU (190 mg, 0.50 mmol) then stirred at r.t. overnight. The crude mixture was diluted with water (10 mL) and extracted into DCM (10 mL). The DCM was then evaporated and the crude product was purified by preparative HPLC (SunFire C18 column, 5 μm, 50 mm×19 mm at 25 mL/min). Decreasingly polar ratios of water and MeCN containing 0.1% formic acid were used as a mobile phase. Fractions containing the desired mass were combined, evaporated and passed through an SCX column washed with MeOH then eluted with 2M NH₃ in MeOH. The basic fraction was evaporated to give the mixture of diastereoisomers as an off-white solid (35 mg). The diastereoisomers were separated by preparative HPLC (Lux C4 column, 20 μm, 50 mm×250 mm, 100% MeOH at 120 mL/min) to give:

First eluted isomer example 11(a) N-[5-[[(3R)-1-(5-chloropyridazin-3-yl)pyrrolidin-3-yl]amino]-1,3,4-thiadiazol-2-yl]-2-methoxy-2-(4-methoxyphenyl)acetamide (12 mg, 7.5%)¹H NMR (400 MHz, DMSO, 30° C.) 2.03-2.13 (1H, m), 2.23-2.33 (1H, m), 3.49-3.63 (3H, m), 3.75 (3H, s), 3.76-3.80 (1H, m), 4.33-4.42 (1H, m), 4.89 (1H, s), 6.90-6.96 (2H, m), 7.10 (1H, d), 7.34-7.41 (2H, m), 7.60 (1H, d), 8.55 (1H, d), 12.10 (1H, s); m/z: ES⁺ [M+H]⁺ 476. plus 3H obscured by water peak at 3.3 ppm Second eluted isomer example 11(b) N-[5-[[(3R)-1-(5-chloropyridazin-3-yl)pyrrolidin-3-yl]amino]-1,3,4-thiadiazol-2-yl]-2-methoxy-2-(4-methoxyphenyl)acetamide (15 mg, 9.4%). ¹H NMR (400 MHz, DMSO, 30° C.) 2.01-2.12 (1H, m), 2.22-2.31 (1H, m), 3.27 (3H, s), 3.47-3.62 (3H, m), 3.75 (3H, s), 3.76-3.79 (1H, m), 4.33-4.42 (1H, m), 4.86 (1H, s), 6.89-6.96 (2H, m), 7.10 (1H, d), 7.34-7.41 (2H, m), 7.51 (1H, d), 8.55 (1H, d). m/z: ES⁺[M+H]⁺ 476.

Example 12

(2S)-N-[5-[[(3R)-1-(5-Chloropyridazin-3-yl)pyrrolidin-3-yl]amino]-1,3,4-thiadiazol-2-yl]-2-methoxy-2-phenyl-acetamide

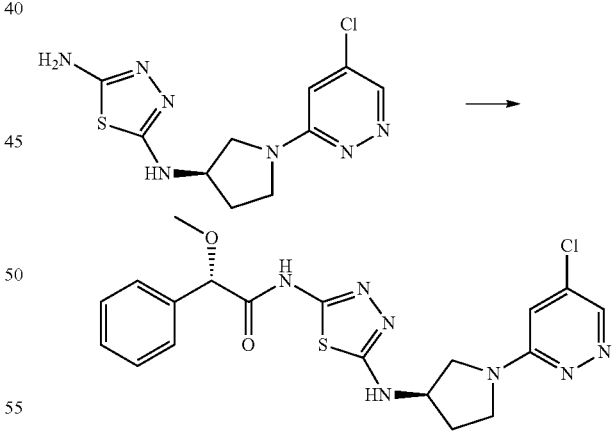

DIPEA (0.04 mL, 0.20 mmol), N2-[(3R)-1-(5-chloropyridazin-3-yl)pyrrolidin-3-yl]-1,3,4-thiadiazole-2,5-diamine (Intermediate 9, 40 mg, 0.13 mmol) and (2S)-2-methoxy-2-phenylacetic acid (20 mg, 0.13 mmol) were added to a solution of HATU (61 mg, 0.16 mmol) in DMF (2 mL). The mixture was stirred at 25° C. for 18 hrs. This was then diluted with water (5 mL) and then extracted into DCM (10 mL) and evaporated under reduced pressure. The crude product was purified by preparative HPLC (SunFire C18 column, 5 μm, 50 mm×19 mm at 25 mL/min). Decreasingly polar ratios of water and MeCN containing 0.1% formic acid were used as a mobile phase. Appropriate fractions were then evaporated and re-purified by basic preparative chromatography. An XBridge column (5 micron, C18, 50×19 mm) was used. Decreasingly polar ratios of water water containing 0.1% ammonium hydroxide and acetonitrile were used as the mobile phase. The pure fractions were then evaporated and dried in the vacuum oven to afford:

(2S)-N-[5-[[(3R)-1-(5-chloropyridazin-3-yl)pyrrolidin-3-yl]amino]-1,3,4-thiadiazol-2-yl]-2-methoxy-2-phenyl-acetamide as a white solid (15 mg, 25%). $^1$H NMR (400 MHz, DMSO-d6, 25° C.) δ 1.98-2.14 (1H, m), 2.17-2.36 (1H, m), 3.30 (3H, s), 3.44-3.64 (3H, m), 3.69-3.81 (1H, m), 4.28-4.42 (1H, m), 4.96 (1H, s), 7.11 (1H, d), 7.30-7.47 (5H, m), 7.69 (1H, d), 8.55 (1H, d), 12.24 (1H, s). m/z: ES$^+$ [M+H]$^+$ 446, 448.

Example 13

(2S)-2-Methoxy-N-[5-[[(3R)-1-(5-methylpyridazin-3-yl)pyrrolidin-3-yl]amino]-1,3,4-thiadiazol-2-yl]-2-phenyl-acetamide

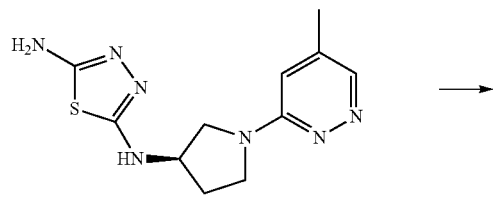

→

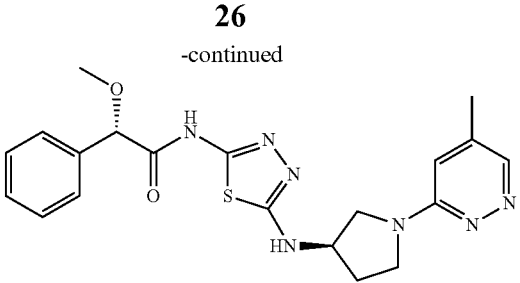

DIPEA (0.09 mL, 0.54 mmol), HATU (164 mg, 0.43 mmol) and (2S)-2-methoxy-2-phenylacetic acid (60 mg, 0.36 mmol) were added to a solution of N2-[(3R)-1-(5-methylpyridazin-3-yl)pyrrolidin-3-yl]-1,3,4-thiadiazole-2,5-diamine (Intermediate 7, 100 mg, 0.36 mmol) in DMF (2 mL). The mixture was stirred at room temperature for 2 hrs. This was then diluted with water (5 mL), extracted into DCM (10 mL) and evaporated under reduced pressure. The crude product was purified by preparative HPLC (SunFire C18 column, 5 µm, 50 mm×19 mm at 25 mL/min). Decreasingly polar ratios of water and MeCN containing 0.1% formic acid were used as a mobile phase. The fractions collected were then passed down an SCX cartridge washing with methanol before eluting with 2M ammonia in methanol. The ammonia in methanol was evaporated and the residue was dried in a vacuum oven to afford:

(2S)-2-methoxy-N-[5-[[(3R)-1-(5-methylpyridazin-3-yl)pyrrolidin-3-yl]amino]-1,3,4-thiadiazol-2-yl]-2-phenyl-acetamide as a white solid (28 mg, 18%). $^1$H NMR (400 MHz, DMSO-d6, 25° C.) δ 2.01-2.10 (1H, m), 2.19 (3H, s), 2.22-2.34 (1H, m), 3.31 (3H, s), 3.42-3.60 (3H, m), 3.70-3.74 (1H, m), 4.30-4.42 (1H, m), 4.98 (1H, s), 6.70 (1H, s), 7.30-7.42 (3H, m), 7.43-7.49 (2H, m), 7.70 (1H, d), 8.35 (1H, s), 12.26 (1H, s). m/z: ES$^+$ [M+H]$^+$ 426

Additional Examples

The compounds of the following Examples were prepared in a similar fashion to the Examples above.

| Example no. | Name | MS data |
| --- | --- | --- |
| 14 | (2S)-2-methoxy-N-[5-[[(3R)-1-(6-methylpyridazin-3-yl)pyrrolidin-3-yl]amino]-1,3,4-thiadiazol-2-yl]-2-phenyl-acetamide | m/z: ES+ [M + H]+ 425 |
| 15 | 2-ethoxy-2-(4-methoxyphenyl)-N-[5-[[(3R)-1-(6-methylpyridazin-3-yl)pyrrolidin-3-yl]amino]-1,3,4-thiadiazol-2-yl]acetamide | m/z: ES+ [M + H]+ 470 |
| 16 | 2-ethoxy-2-(4-methoxyphenyl)-N-[5-[[(3R)-1-(6-methylpyridazin-3-yl)pyrrolidin-3-yl]amino]-1,3,4-thiadiazol-2-yl]acetamide | m/z: ES+ [M + H]+ 470 |
| 17 | N-[5-[[(3R)-1-(6-fluoropyridazin-3-yl)pyrrolidin-3-yl]amino]-1,3,4-thiadiazol-2-yl]-2-methoxy-2[3-(trifluoromethoxy)phenyl]acetamide | m/z (ES+), [M + H]+ = 514 |
| 18 | N-[5-[[(3R)-1-(6-fluoropyridazin-3-yl)pyrrolidin-3-yl]amino]-1,3,4-thiadiazol-2-yl]-2-methoxy-2[3-(trifluoromethoxy)phenyl]acetamide | m/z (ES+), [M + H]+ = 514 |
| 19 | 2-(4-fluorophenyl)-N-[5-[[(3R)-1-(6-fluoropyridazin-3-yl)pyrrolidin-3-yl]amino]-1,3,4-thiadiazol-2-yl]-2-methoxy-acetamide | m/z (ES+), [M + H]+ = 448; |
| 20 | 2-(4-fluorophenyl)-N-[5-[[(3R)-1-(6-fluoropyridazin-3-yl)pyrrolidin-3-yl]amino]-1,3,4-thiadiazol-2-yl]-2-methoxy-acetamide | m/z (ES+), [M + H]+ = 448 |
| 21 | N-[5-[[(3R)-1-(6-fluoropyridazin-3-yl)pyrrolidin-3-yl]amino]-1,3,4-thiadiazol-2-yl]-2-methoxy-2-(4-methoxyphenyl)acetamide | m/z (ES−), [M − H]− = 458 |

-continued

| Example no. | Name | MS data |
|---|---|---|
| 22 | N-[5-[[(3R)-1-(6-fluoropyridazin-3-yl)pyrrolidin-3-yl]amino]-1,3,4-thiadiazol-2-yl]-2-methoxy-2-(4-methoxyphenyl)acetamide | m/z (ES−), [M − H]− = 458 |
| 23 | 2-(4-fluoro-3-methoxy-phenyl)-N-[5-[[(3R)-1-(6-fluoropyridazin-3-yl)pyrrolidin-3-yl]amino]-1,3,4-thiadiazol-2-yl]-2-methoxy-acetamide | m/z (ES+), [M + H]+ = 478 |
| 24 | 2-(4-fluoro-3-methoxy-phenyl)-N-[5-[[(3R)-1-(6-fluoropyridazin-3-yl)pyrrolidin-3-yl]amino]-1,3,4-thiadiazol-2-yl]-2-methoxy-acetamide | m/z (ES+), [M + H]+ = 478 |
| 25 | 2-ethoxy-2-(4-fluorophenyl)-N-[5-[[(3R)-1-(6-fluoropyridazin-3-yl)pyrrolidin-3-yl]amino]-1,3,4-thiadiazol-2-yl]acetamide | m/z (ES+), [M + H]+ = 462 |
| 26 | 2-ethoxy-2-(4-fluorophenyl)-N-[5-[[(3R)-1-(6-fluoropyridazin-3-yl)pyrrolidin-3-yl]amino]-1,3,4-thiadiazol-2-yl]acetamide | m/z (ES+), [M + H]+ = 462 |
| 27 | 2-ethoxy-2-(4-fluorophenyl)-N-[5-[[(3R)-1-(6-methylpyridazin-3-yl)pyrrolidin-3-yl]amino]-1,3,4-thiadiazol-2-yl]acetamide | m/z (ES+), [M + H]+ = 458 |
| 28 | 2-ethoxy-2-(4-fluorophenyl)-N-[5-[[(3R)-1-(6-methylpyridazin-3-yl)pyrrolidin-3-yl]amino]-1,3,4-thiadiazol-2-yl]acetamide | m/z (ES+), [M + H]+ = 458 |
| 29 | 2-methoxy-2-(4-methoxyphenyl)-N-[5-[[(3R)-1-(6-methylpyridazin-3-yl)pyrrolidin-3-yl]amino]-1,3,4-thiadiazol-2-yl]acetamide | m/z (ES+), [M + H]+ = 456 |
| 30 | 2-methoxy-2-(4-methoxyphenyl)-N-[5-[[(3R)-1-(6-methylpyridazin-3-yl)pyrrolidin-3-yl]amino]-1,3,4-thiadiazol-2-yl]acetamide | m/z (ES+), [M + H]+ = 456 |
| 31 | (2S)-2-methoxy-N-[5-[[(3R)-1-(5-methylpyridazin-3-yl)pyrrolidin-3-yl]amino]-1,3,4-thiadiazol-2-yl]-2-phenyl-acetamide | m/z (ES+), [M + H]+ = 426 |
| 32 | (2S)-N-[5-[[(3R)-1-(5-chloropyridazin-3-yl)pyrrolidin-3-yl]amino]-1,3,4-thiadiazol-2-yl]-2-methoxy-2-phenyl-acetamide | m/z (ES+), [M + H]+ = 446 |

Example 33(a) and 33(b)

(2R)-2-methoxy-2-(4-methoxyphenyl)-N-[5-[[(3R)-1-(5-methylpyridazin-3-yl)pyrrolidin-3-yl]amino]-1,3,4-thiadiazol-2-yl]acetamide and (2S)-2-methoxy-2-(4-methoxyphenyl)-N-[5-[[(3R)-1-(5-methylpyridazin-3-yl)pyrrolidin-3-yl]amino]-1,3,4-thiadiazol-2-yl]acetamide

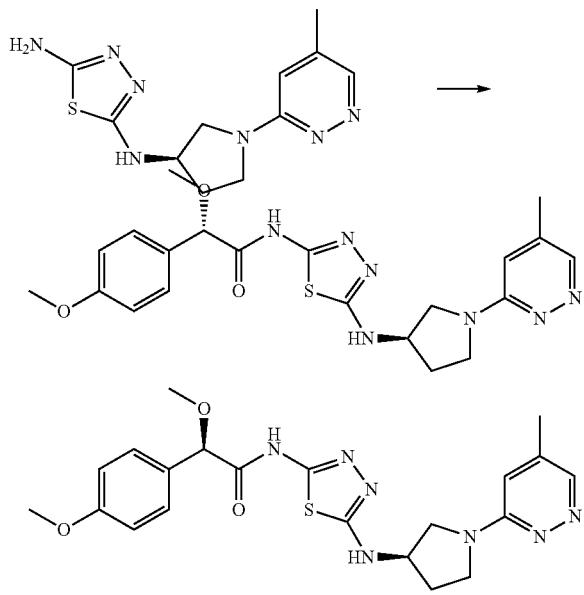

N2-[(3R)-1-(5-methylpyridazin-3-yl)pyrrolidin-3-yl]-1,3,4-thiadiazole-2,5-diamine (Intermediate 7, 0.05 g, 0.173 mmol) and N-[(Dimethylamino)(3H-[1,2,3]triazolo[4,5-b]pyridin-3-yloxy)methylidene]-N-methylmethylaminium hexafluorophosphate, HATU (0.08 g, 0.208 mmol) were dissolved in DMF (2 mL) at r.t under $N_2$. The mixture was stirred for 5 mins before addition of 2-methoxy-2-(4-methoxyphenyl)acetic acid (Intermediate 21, 0.04 g, 0.173 mmol) and DIPEA (0.05 mL, 0.26 mmol). The reaction was stirred at r.t overnight under $N_2$. The crude mixture was passed through a 5 g SCX column washed with MeOH then eluted with 2M $NH_3$ in MeOH. The basic fraction was evaporated under reduced pressure to give the impure product as an orange gum. The crude product was purified by preparative HPLC (SunFire C18 column, 5 µm, 50 mm×19 mm at 25 mL/min). Decreasingly polar ratios of water and MeCN containing 0.1% formic acid were used as a mobile phase. Fractions containing the desired mass were combined, evaporated under reduced pressure and passed through a 5 g SCX column, washed with MeOH, then eluted with 2M $NH_3$ in MeOH. The basic fraction was evaporated under reduced pressure to give the mixture of diastereoisomers as an off-white solid. The diastereoisomers were separated by preparative chiral SFC (Lux C1 column, 5 µm, 21.2 mm×250 mm, flow rate 50 mL/min at a wavelength of 210 nm with 40:60 MeOH:$CO_2$+0.1% $NH_3$ as eluent) to give:

First eluted isomer example 33(a) 2-methoxy-2-(4-methoxyphenyl)-N-[5-[[(3R)-1-(5-methylpyridazin-3-yl)pyrrolidin-3-yl]amino]-1,3,4-thiadiazol-2-yl]acetamide (6.6 mg, 8%). $^1$H NMR (400 MHz, DMSO-d6) δ 12.18 (1H, s), 8.36 (1H, d), 7.68 (1H, d), 7.41-7.34 (2H, m), 6.99-6.90 (2H, m), 6.71 (1H, s), 4.90 (1H, s), 4.45-4.30 (1H, m), 3.74 (3H, s), 3.64-3.37 (4H, m), 3.27 (3H, s), 2.35-2.23 (1H, m), 2.20 (3H, s), 2.09-1.98 (1H, m). m/z: ES+ [M+H]+ 456.

Second eluted example 33(b) 2-methoxy-2-(4-methoxyphenyl)-N-[5-[[(3R)-1-(5-methylpyridazin-3-yl)pyrrolidin-3-yl]amino]-1,3,4-thiadiazol-2-yl]acetamide (5.7 mg, 6%). $^1$H NMR (400 MHz, DMSO-d6) δ 12.18 (1H, s), 8.35 (1H, d), 7.66 (1H, d), 7.37 (2H, d), 6.94 (2H, d), 6.70 (1H, d), 4.89 (1H, s), 4.43-4.29 (1H, m), 3.74 (3H, s), 3.73-3.69 (1H, m), 3.60-3.45 (3H, m), 3.27 (3H, s), 2.34-2.23 (1H, m), 2.20 (3H, s), 2.10-2.01 (1H, m). m/z: ES⁺ [M+H]⁺ 456.

Intermediate 1

N2-[(3R)-1-(6-Methylpyridazin-3-yl)pyrrolidin-3-yl]-1,3,4-thiadiazole-2,5-diamine

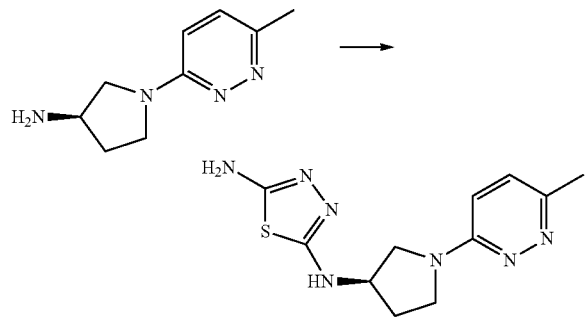

5-Bromo-1,3,4-thiadiazol-2-amine (912 mg, 5.07 mmol), (3R)-1-(6-methylpyridazin-3-yl)pyrrolidin-3-amine (Intermediate 2, 860 mg, 4.83 mmol) and DIPEA (0.924 mL, 5.31 mmol) were dissolved in DMF (10 mL). The reaction was heated to 100° C. for 1 h then left at r.t. overnight. The crude product was purified by ion exchange chromatography, using an SCX column. The desired product was eluted from the column using 1M NH₃ in MeOH and pure fractions were evaporated to dryness to afford crude product. This was dissolved in DCM/MeOH, adsorbed onto silica and purified by FCC (SiO₂, 0 to 20% MeOH in DCM). Pure fractions were evaporated to dryness to afford N2-[(3R)-1-(6-methylpyridazin-3-yl)pyrrolidin-3-yl]-1,3,4-thiadiazole-2,5-diamine (350 mg, 26%) as a brown gum. m/z: ES⁺ [M+H]⁺ 278.

Intermediate 2

(3R)-1-(6-Methylpyridazin-3-yl)pyrrolidin-3-amine

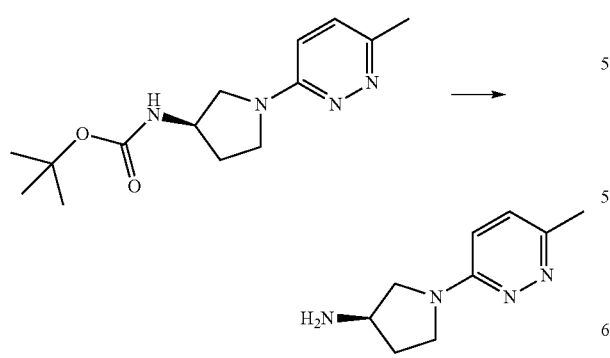

Trifluoroacetic acid (12 mL) was added to tert-butyl N-[(3R)-1-(6-methylpyridazin-3-yl)pyrrolidin-3-yl]carbamate (Intermediate 3, 2.1 g, 7.54 mmol), in DCM (60 mL) at 21° C. under nitrogen. The resulting solution was stirred at 21° C. for 2 h. The crude product was purified by ion exchange chromatography, using an SCX column. The desired product was eluted from the column using 7M NH₃ in MeOH and pure fractions were evaporated to dryness to afford (3R)-1-(6-methylpyridazin-3-yl)pyrrolidin-3-amine (1.6 g, 119%) as a yellow oil which solidified on standing. ¹H NMR (400 MHz, DMSO-d6, 27° C.) δ 1.56-1.8 (1H, m), 2.04 (1H, m), 2.39 (3H, s), 3.07 (1H, m), 3.37-3.43 (1H, m), 3.47-3.66 (3H, m), 4.08 (1H, s), 6.73 (1H, d), 7.19 (1H, d). m/z: ES⁺ [M+H]⁺ 179.

Intermediate 3 tert-Butyl N-[(3R)-1-(6-methylpyridazin-3-yl)pyrrolidin-3-yl]carbamate

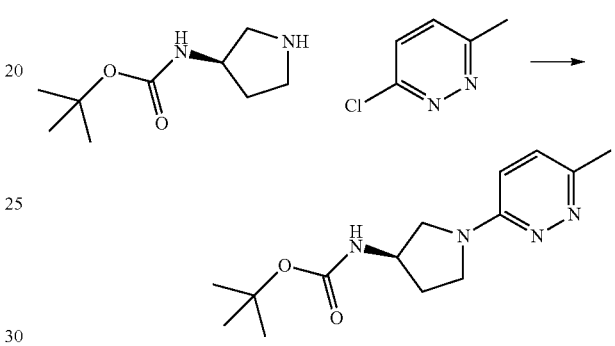

A mixture of DIPEA (8.49 mL, 48.62 mmol), tert-butyl N-[(3R)-pyrrolidin-3-yl]carbamate (3.62 g, 19.45 mmol), 3-chloro-6-methylpyridazine (2.5 g, 19.45 mmol) and n-butanol (30 mL) was stirred at 130° C. for 12 h then left to cool over the weekend. The reaction mixture was evaporated and the crude product was purified by FCC (SiO₂, 0 to 10% 1M NH₃ in MeOH in EtOAc). Pure fractions were evaporated to dryness to afford tert-butyl N-[(3R)-1-(6-methylpyridazin-3-yl)pyrrolidin-3-yl]carbamate (2.1 g, 38.8%) as a yellow solid. ¹H NMR (400 MHz, DMSO-d6, 27° C.) δ 1.39 (9H, s), 1.88 (1H, m), 2.14 (1H, m), 2.40 (3H, s), 3.23 (1H, m), 3.37-3.45 (1H, m), 3.47-3.58 (1H, m), 3.61 (1H, m), 3.99-4.2 (1H, m), 6.77 (1H, d), 7.20 (2H, m); m/z: ES⁺ [M+H]⁺ 279.

Intermediate 4

N2-[(3R)-1-(6-Fluoropyridazin-3-yl)pyrrolidin-3-yl]-1,3,4-thiadiazole-2,5-diamine

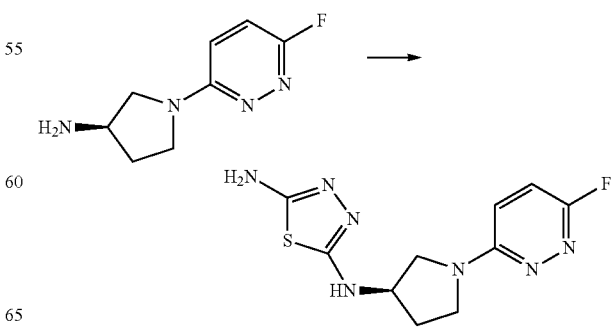

DIPEA (3.48 mL, 19.96 mmol) was added to 5-bromo-1,3,4-thiadiazol-2-amine (1.797 g, 9.98 mmol) and (3R)-1-(6-fluoropyridazin-3-yl)pyrrolidin-3-amine (Intermediate 5, 2 g, 10.98 mmol) in anhydrous DMF (40 mL) at r.t. The resulting solution was stirred at 80° C. for 4 h. The crude product was purified by ion exchange chromatography, using an SCX column. The desired product was eluted from the column using 1M NH₃ in MeOH and pure fractions were evaporated to dryness to afford N2-[(3R)-1-(6-fluoropyridazin-3-yl)pyrrolidin-3-yl]-1,3,4-thiadiazole-2,5-diamine (2.9 g, 103%) as a brown solid. ¹H NMR (400 MHz, DMSO-d6, 30° C.) δ 1.90-2.12 (1H, m), 2.23 (1H, dtd), 3.42 (1H, dd), 3.47-3.61 (2H, m), 3.69 (1H, dd), 4.25 (1H, dq), 6.25 (2H, s), 7.04 (1H, d), 7.14 (1H, dd), 7.33 (1H, dd). m/z: ES⁺ [M+H]⁺ 282.

Intermediate 5

(3R)-1-(6-Fluoropyridazin-3-yl)pyrrolidin-3-amine

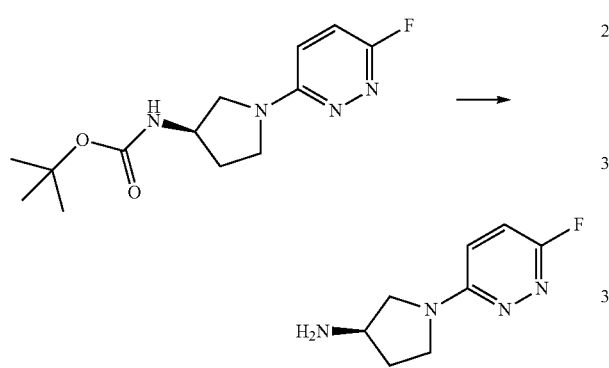

tert-Butyl N-[(3R)-1-(6-fluoropyridazin-3-yl)pyrrolidin-3-yl]carbamate (Intermediate 6, 6 g, 21.25 mmol) was added to DCM (70 mL) and TFA (14.00 mL) at 25° C. The resulting solution was stirred at 25° C. for 4 h. The crude product was purified by ion exchange chromatography, using an SCX column. The desired product was eluted from the column using 1M NH₃ in MeOH and pure fractions were evaporated to dryness to afford (3R)-1-(6-fluoropyridazin-3-yl)pyrrolidin-3-amine (2.0 g, 52%) as a pale yellow gummy solid. ¹H NMR (400 MHz, DMSO-d6, 30° C.) δ 1.55-1.83 (1H, m), 1.98-2.13 (1H, m), 2.89-3.14 (1H, m), 3.29-3.43 (1H, m), 3.54 (3H, ddt), 7.06 (1H, dd), 7.30 (1H, dd). m/z: ES⁺ [M+H]⁺ 183.

Intermediate 6 tert-butyl N-[(3R)-1-(6-Fluoropyridazin-3-yl)pyrrolidin-3-yl]carbamate

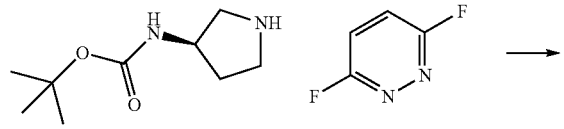

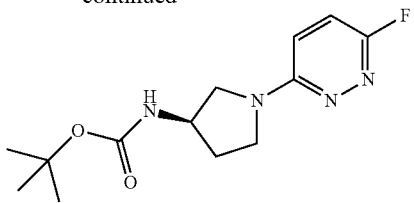

A mixture of 3,6-difluoropyridazine (6.06 g, 52.21 mmol) tert-butyl N-[(3R)-pyrrolidin-3-yl]carbamate (9.72 g, 52.21 mmol), DIPEA (22.80 mL, 130.53 mmol) and n-butanol (140 mL) was stirred at 130° C. for 10 h. The reaction mixture was diluted with EtOAc (750 mL), and washed twice with water (150 mL). The organic layer was dried over Na₂SO₄, filtered and evaporated to afford crude product. This was then dissolved in DCM and the crude product was purified by FCC (SiO₂, 30-65% EtOAc in heptanes). Pure fractions were evaporated to dryness to afford tert-butyl N-[(3R)-1-(6-fluoropyridazin-3-yl)pyrrolidin-3-yl]carbamate (15 g, 102%) as a cream solid. ¹H NMR (400 MHz, CDCl₃, 30° C.) δ 1.46 (9H, s), 1.91-2.13 (1H, m), 2.32 (1H, dq), 3.40 (1H, dd), 3.56-3.72 (2H, m), 3.78 (1H, dd), 4.37 (1H, s), 4.70 (1H, s), 6.78 (1H, dd), 6.98 (1H, dd). m/z: ES⁺ [M+H]⁺ 283.

Intermediate 7

N2-[(3R)-1-(5-Methylpyridazin-3-yl)pyrrolidin-3-yl]-1,3,4-thiadiazole-2,5-diamine

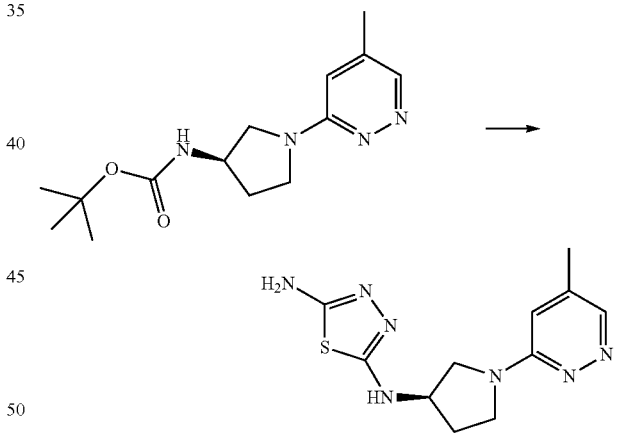

tert-Butyl(3R)-3-[(5-methylpyridazin-3-yl)amino]pyrrolidine-1-carboxylate (Intermediate 8, 200 mg, 0.72 mmol) was dissolved in DCM (5 mL) and treated with TFA (5 mL). It was left to stir at room temperature for 2 hours, then evaporated to dryness to give a yellow oil. This was then dissolved in acetonitrile (5 mL) and treated with DIPEA (0.38 mL, 2.15 mmol) followed by 5-bromo-1,3,4-thiadiazol-2-ylamine (130 mg, 0.72 mmol) and then heated to 80° C. for 3 h. The reaction mixture was evaporated and purified by FCC (SiO₂, 0-10% 2M NH₃ in MeOH in DCM). Fractions containing the product were combined and evaporated to give N2-[(3R)-1-(5-methylpyridazin-3-yl)pyrrolidin-3-yl]-1,3,4-thiadiazole-2,5-diamine (100 mg, 50%). ¹H NMR (400 MHz, DMSO-d6, 25° C.) δ 1.99-2.05 (1H, m), 2.18-2.31 (4H, m), 3.38-3.58 (3H, m), 3.67-3.71 (1H, m), 4.19-

4.30 (1H, m), 6.31 (2H, s), 6.70 (1H, s), 7.09 (1H, d), 8.36 (1H, s). m/z: ES⁺ [M+H]⁺ 278.

Intermediate 8 tert-Butyl(3R)-3-[(6-chloropyridazin-3-yl)amino]pyrrolidine-1-carboxylate

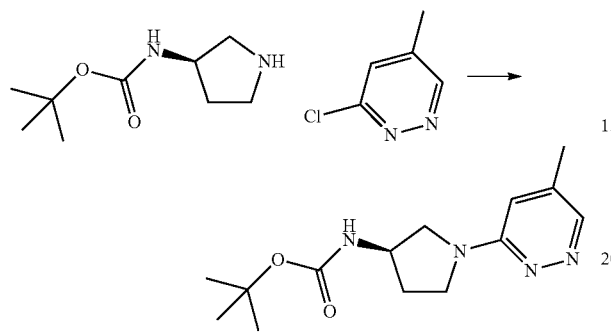

tert-butyl N-[(3R)-pyrrolidin-3-yl]carbamate (250 mg, 1.34 mmol) was dissolved in 1-butanol (2 mL) and treated with 3-chloro-5-methylpyridazine (0.25M in DCM, 2.68 mL, 1.34 mmol) followed by DIPEA (0.48 mL, 2.68 mmol). The mixture was heated to 140° C. for 2 hours. The reaction mixture was cooled to r.t. diluted with water (10 mL) and extracted into DCM (10 mL). The solvent was evaporated and the residue purified by FCC (SiO₂, 0-10% methanol in DCM). The fractions containing the product were combined and evaporated to give tert-butyl N-[(3R)-1-(5-methyl-pyridazin-3-yl)pyrrolidin-3-yl]carbamate (200 mg, 53%). ¹H NMR (400 MHz, DMSO-d6, 25° C.) δ 1.40 (9H, s), 1.85-1.93 (1H, m), 2.07-2.18 (1H, m), 2.20 (3H, s), 3.24-3.28 (1H, m), 3.38-3.48 (1H, m), 3.48-3.59 (1H, m), 3.60-3.65 (1H, m), 4.10-4.15 (1H, m), 6.67 (1H, s), 7.24 (1H, d), 8.35 (1H, d). m/z: ES⁺ [M+H]⁺ 279.

Intermediate 9

N2-[(3R)-1-(5-Chloropyridazin-3-yl)pyrrolidin-3-yl]-1,3,4-thiadiazole-2,5-diamine

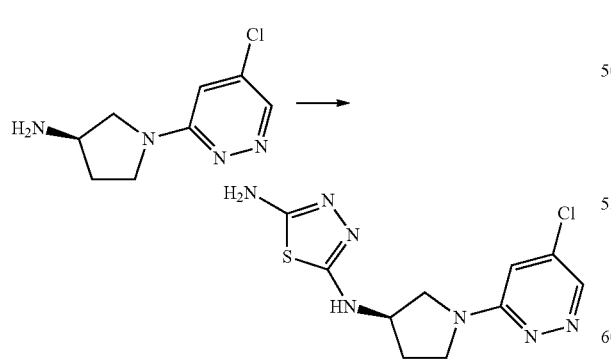

(3R)-1-(5-Chloropyridazin-3-yl)pyrrolidin-3-amine (Intermediate 10, 50 mg, 0.25 mmol) was dissolved in acetonitrile (5 mL) and treated with DIPEA (0.07 mL, 0.38 mmol) followed by 5-bromo-1,3,4-thiadiazol-2-ylamine (50 mg, 0.25 mmol) and heated to 80° C. for 3 h. The reaction mixture was then evaporated and purified by FCC (SiO₂, 0-10% 2M NH₃ in MeOH in DCM). Fractions containing the product were combined and evaporated to give N2-[(3R)-1-(5-chloropyridazin-3-yl)pyrrolidin-3-yl]-1,3,4-thiadiazole-2,5-diamine which was used directly in the next step (50 mg, 66%). m/z: ES⁺ [M+H]⁺ 298, 300.

Intermediate 10

(3R)-1-(5-Chloropyridazin-3-yl)pyrrolidin-3-amine

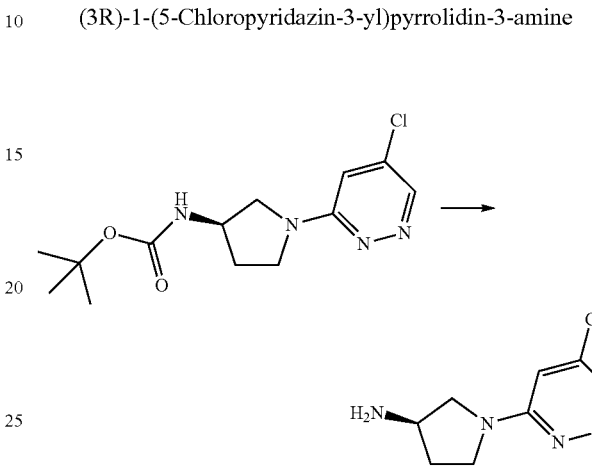

tert-butyl N-[(3R)-1-(5-Chloropyridazin-3-yl)pyrrolidin-3-yl]carbamate (Intermediate 11, 77 mg, 0.25 mmol) was dissolved in DCM (1 mL), treated with TFA (1 mL), and left to stir at r.t. for 2 h. It was then evaporated to dryness and passed down an SCX cartridge washed with methanol and eluted with 2M methanolic ammonia. The basic fraction was evaporated to give (3R)-1-(5-chloropyridazin-3-yl)pyrrolidin-3-amine, which was used directly in the next step (50 mg, 99%). m/z: ES⁺ [M+H]⁺ 199, 201.

Intermediate 11 tert-Butyl N-[(3R)-1-(5-chloropyridazin-3-yl)pyrrolidin-3-yl]carbamate

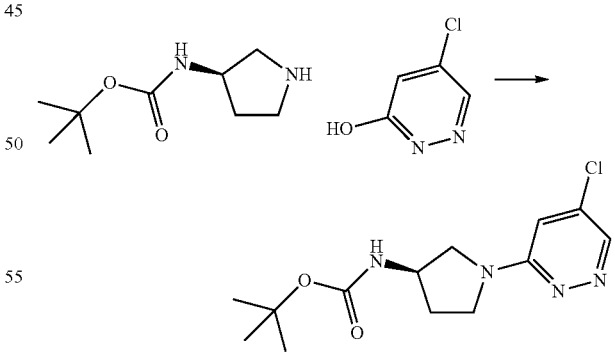

5-Chloropyridazin-3-ol (0.2 g, 1.53 mmol) was dissolved in DCM (2 mL) and triethylamine (0.47 mL, 3.37 mmol) and cooled to −20° C. It was then treated, dropwise, with trifluoromethanesulphonic anhydride (1M in DCM, 3.22 mL, 3.22 mmol). The reaction mixture was then allowed to return slowly to room temperature. It was quenched by addition of water (10 mL) and extracted into DCM (10 mL). The organics were washed with 1M HCl (10 mL) dried (MgSO$_4$), filtered and evaporated to give (5-chloro-pyridazin-3-yl)trifluoromethanesulfonate. This was then dissolved in DMF (2 mL) and cooled to 0° C. before being treated with triethylamine (0.21 mL, 1.53 mmol) and tert-butyl N-[(3R)-pyrrolidin-3-yl]carbamate (290 mg, 1.53 mmol). It was then allowed to return to room temperature, diluted with water (20 mL) and extracted into DCM (20 mL). The organics were evaporated and purified by FCC (SiO$_2$, 0-10% MeOH in DCM). Fractions containing the product were combined and evaporated to give tert-butyl N-[(3R)-1-(5-chloropyridazin-3-yl)pyrrolidin-3-yl]carbamate, (77 mg, 17%). $^1$H NMR (400 MHz, DMSO-d6, 25° C.) δ 1.40 (9H, s), 1.84-1.99 (1H, m), 2.05-2.20 (1H, m), 3.32-3.34 (1H, m), 3.42-3.60 (2H, m), 3.60-3.73 (1H, m), 4.00-4.28 (1H, m), 7.08 (1H, d), 7.26 (1H, d), 8.55 (1H, d). m/z: ES$^+$ [M+H]$^+$ 299, 301.

Intermediate 12

(2S)-2-Methoxy-2-(3-methoxyphenyl)acetic acid

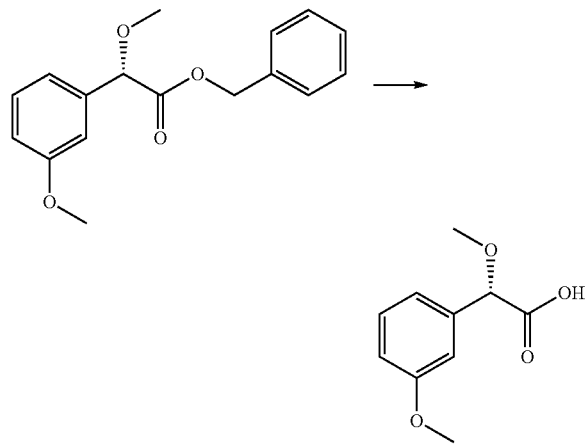

Benzyl(2S)-2-methoxy-2-(3-methoxyphenyl)acetate (Intermediate 13(a), 7.85 g, 27.42 mmol) and 10% Pd on C (1 g, 27.42 mmol) in ethanol (250 mL) was stirred under an atmosphere of hydrogen at ambient temperature for 4 hours. The reaction mixture was filtered through celite which was washed with MeOH. The organics were then evaporated to give (2S)-2-methoxy-2-(3-methoxyphenyl)acetic acid as a clear oil (6.0 g, 112%, contains some MeOH). $^1$H NMR (400 MHz, DMSO-d6, 30° C.) δ 3.29 (3H, s), 3.74 (3H, s), 4.72 (1H, s), 6.77-7.06 (3H, m), 7.28 (1H, t), 12.77 (1H, s).

Intermediate 13(a)

Benzyl(2S)-2-methoxy-2-(3-methoxyphenyl)acetate

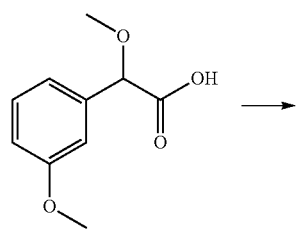

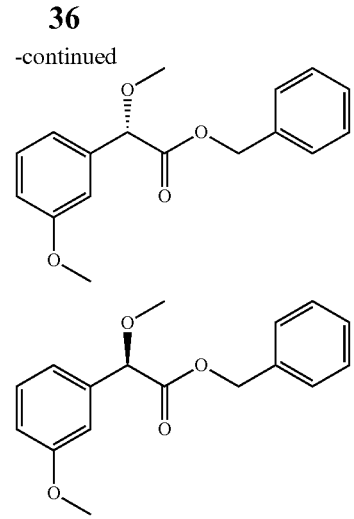

Benzyl bromide (7.81 mL, 65.75 mmol) was added dropwise to 2-methoxy-2-(3-methoxyphenyl)acetic acid (Intermediate 14, 10.75 g, 54.79 mmol), potassium carbonate (11.36 g, 82.19 mmol) in DMF (200 mL) at 21° C. under nitrogen. The resulting mixture was stirred at 85° C. for 4 hours then was left stirring at ambient temperature over the weekend. The reaction mixture was diluted with EtOAc (600 mL), and washed twice with water (200 mL). The organic layer was dried over Na$_2$SO$_4$, filtered and evaporated to afford crude product which was purified by FCC (SiO$_2$ 10-25% EtOAc in heptanes). Pure fractions were evaporated to dryness to afford a colourless oil. (10.5 g).

Benzyl bromide (5.59 mL, 47.09 mmol) was added dropwise to 2-methoxy-2-(3-methoxyphenyl)acetic acid (Intermediate 14, 7.7 g, 39.25 mmol), potassium carbonate (8.14 g, 58.87 mmol) in DMF (150 mL) at 21° C. under nitrogen. The resulting mixture was stirred at 85° C. for 4 hours, then left stirring at ambient temperature over the weekend.

The reaction was then heated at 85° C. for a further 4 hours before being cooled to RT. The reaction mixture was diluted with EtOAc (500 mL), and washed twice with water (200 mL). The organic layer was dried over Na$_2$SO$_4$, filtered and evaporated to afford crude product. The crude product was purified by FCC (SiO$_2$ 10-25% EtOAc in heptanes). Pure fractions were evaporated to dryness to afford a pale yellow oil (6 g). Product from the two reactions were combined and the enantiomers separated by chiral HPLC. (Chiralpak OD column, 20 µm, 100 mm×250 mm, using a 95/5 mixture of Heptane:EtOH as eluents at 250 mL/min). Fractions containing the desired compound were evaporated to dryness to afford:

First eluted isomer Intermediate 13(a) benzyl(2S)-2-methoxy-2-(3-methoxyphenyl)acetate (7.86 g, 39%). $^1$H NMR (400 MHz, DMSO-d6, 27° C.) δ 3.37 (3H, s), 3.78 (3H, s), 5.02 (1H, s), 5.20 (2H, s), 6.75-7.10 (3H, m), 7.20-7.52 (6H, m).

Second eluted isomer Intermediate 13(b) benzyl(2R)-2-methoxy-2-(3-methoxyphenyl)acetate (7.9 g, 39%). $^1$H NMR (400 MHz, DMSO-d6, 27° C.) δ 3.37 (3H, s), 3.78 (3H, s), 5.02 (1H, s), 5.20 (2H, s), 6.75-7.10 (3H, m), 7.20-7.52 (6H, m).

Intermediate 14

2-Methoxy-2-(3-methoxyphenyl)acetic acid

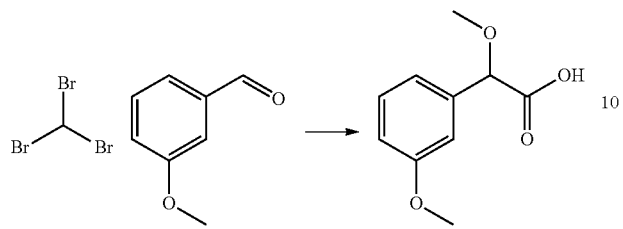

A solution of potassium hydroxide (2.267 g, 40.40 mmol) in MeOH (10 mL) was added over 2 h in small portions to a stirred mixture of 3-methoxybenzaldehyde (1 g, 7.34 mmol) and bromoform (0.771 mL, 8.81 mmol) in MeOH (5.00 mL) at 0° C. The mixture was then allowed to warm to r.t. and left to stir overnight. The solids were filtered under reduced pressure, rinsing the solids with MeOH (15 mL). The filtrate was evaporated to a thick white paste then re-dissolved in water (50 mL). This was then washed with Et$_2$O (50 mL) and then the aqueous portion was acidified to pH 2 (~5 mL 2M HCl solution). The aqueous phase was then extracted with EtOAc (3×50 mL). The combined organics were dried over MgSO$_4$ and filtered then solvents were evaporated under reduced pressure to give 2-methoxy-2-(3-methoxyphenyl)acetic acid as a yellow oil (1.4 g, 97%). $^1$H NMR (400 MHz, DMSO-d6, 30° C.) δ 3.18 (3H, s), 3.75 (3H, s), 4.74 (1H, s), 6.82-7.05 (3H, m), 7.29 (1H, m), 12.78 (1H, s).

Intermediate 15

2-Ethoxy-2-(3-methoxyphenyl)acetic acid

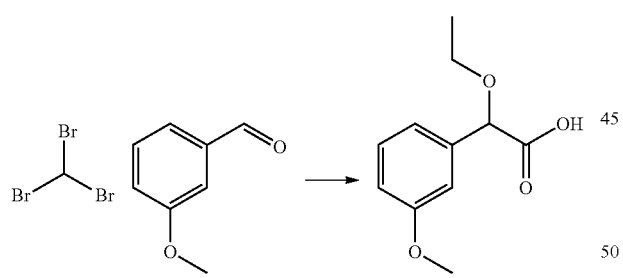

To a stirred mixture of 3-methoxybenzaldehyde (5.0 g, 36.72 mmol) and bromoform (3.85 mL, 44.06 mmol) in ethanol (40 mL) at 0° C. was added dropwise over a 1 hour period a solution of potassium hydroxide (11.33 g, 201.98 mmol) in ethanol (60 mL). After the addition was complete the mixture was left to stir at r.t. overnight. A precipitate had formed which was removed by filtration, and the filtrate was evaporated to give a paste which was taken up in water (100 mL) and extracted with EtOAc (2×100 mL). The aqueous phase was then acidified to pH=2 with 2M HCl and extracted with EtOAc (2×100 mL). The combined organics were dried (MgSO$_4$), filtered and evaporated to give a pale brown oil. This was absorbed onto silica and was purified by FCC (SiO$_2$, 5% MeOH in DCM) to give 2-ethoxy-2-(3-methoxyphenyl)acetic acid (3.1 g, 40%) as a pale brown oil. $^1$H NMR (400 MHz, CDCl$_3$, 21° C.) δ 1.28 (3H, t), 2.09 (1H, s), 3.64-3.52 (2H, m), 3.81 (3H, s) 4.86 (1H, s), 6.89 (1H, ddd), 6.99 (1H, m), 7.03 (1H, m), 7.29 (1H, t). m/z: ES$^-$ [M−H]$^-$ 209.

Intermediate 16

2-(4-Fluorophenyl)-2-methoxy-acetic acid

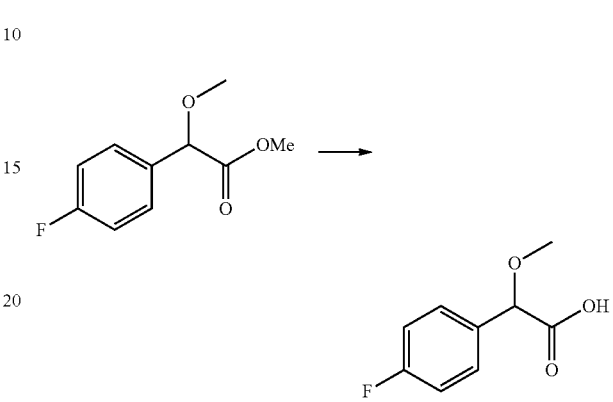

Methyl 2-(4-fluorophenyl)-2-methoxy-acetate (Intermediate 17, 1.32 g, 6.66 mmol) was dissolved in methanol (24 mL) and stirred at r.t. A solution of potassium hydroxide (0.45 g, 7.992 mmol) in methanol (12 mL) was added, and the mixture stirred at r.t for 5 h. The mixture was evaporated to dryness, partitioned between water and EtOAc (70 mL each). The aqueous was washed with EtOAc (70 mL) then acidified with 2N hydrochloric acid to pH 2. It was then extracted with EtOAc (2×100 mL). The organics were dried (MgSO$_4$) and evaporated to give 2-(4-fluorophenyl)-2-methoxy-acetic acid as a clear gum (1.16 g, 94%). $^1$H NMR (400 MHz, CDCl$_3$) 3.42 (3H, s) 4.77 (1H, s), 7.10-7.04 (2H, m), 7.44-7.40 (2H, m).

Intermediate 17

Methyl 2-(4-fluorophenyl)-2-methoxyacetate

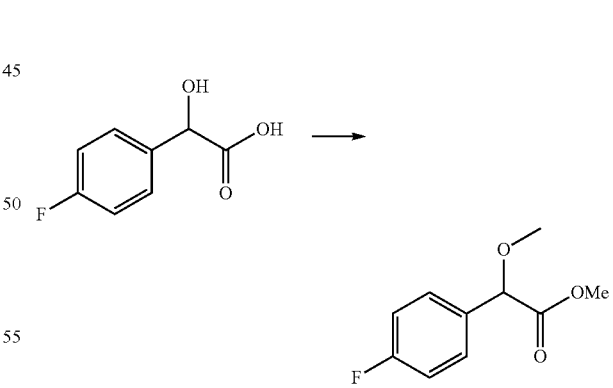

Caesium carbonate (7.64 g, 23.45 mmol) was dissolved in DMF (20 mL) at r.t. iodomethane (2.4 mL, 38.55 mmol) was added, followed by 2-(4-fluorophenyl)-2-hydroxyacetic acid (2.0 g, 11.75 mmol), and the mixture stirred for 48 h at r.t. The DMF was evaporated under reduced pressure and the residue was partitioned between EtOAc and water (75 mL each). The organics were washed with water (75 mL), dried (MgSO$_4$), evaporated under reduced pressure and purified by FCC (SiO$_2$, 3:1 cyclohexane:EtOAc). Pure fractions were evaporated to dryness to afford methyl 2-(4-fluorophenyl)-2-methoxyacetate (1.68 g, 72%) as a colourless oil. ¹H NMR (400 MHz, CDCl₃, 20° C.) δ 3.40 (3H, s), 3.72 (3H, s), 4.76 (1H, s), 7.09-7.03 (2H, m), 7.44-7.40 (2H, m).

Intermediate 18

2-(4-Fluoro-3-methoxy-phenyl)-2-methoxy-acetic acid

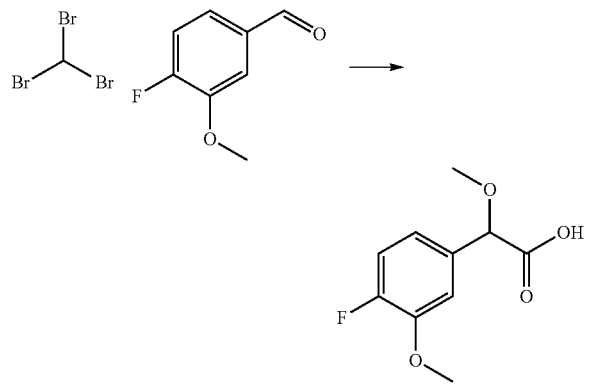

To a stirred mixture of 4-fluoro-3-methoxy-benzaldehyde (1.0 g, 6.48 mmol) and bromoform (0.68 mL, 7.785 mmol) in MeOH (10 mL) at 0° C. was added, dropwise over 1 h, a solution of potassium hydroxide (2.0 g, 35.682 mmol) in MeOH (20 mL). After addition the mixture was stirred and warmed to r.t. overnight. The resulting precipitate was removed by filtration. The filtrate was evaporated to give a paste which was taken up in water (100 mL) and extracted with EtOAc (2×100 mL). The aqueous phase was then acidified to pH=2 with 2N HCl. It was extracted with EtOAc (2×100 mL). The combined organics were dried (MgSO₄), filtered and evaporated under reduced pressure to afford crude product. The crude product was further purified by FCC (SiO₂, 0-5% MeOH in DCM) to give 2-(4-fluoro-3-methoxy-phenyl)-2-methoxy-acetic acid (0.66 g, 47%) as a colourless oil. ¹H NMR (400 MHz, CDCl₃, 30° C.) δ 3.43 (3H, s), 3.90 (3H, s), 4.75 (1H, s), 6.95-7.00 (1H, m), 7.10-7.04 (2H, m). m/z: ES⁻ [M−H]⁻ 213.

Intermediate 19

2-Methoxy-2-[3-(trifluoromethoxy)phenyl]acetic acid

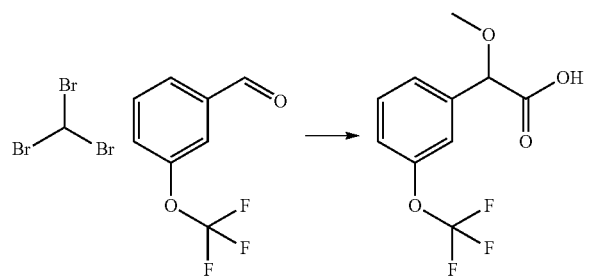

A solution of potassium hydroxide (1.851 g, 33.00 mmol) in MeOH (10 mL) was added over 2 h in small portions to a stirred mixture of 3-(trifluoromethoxy)benzaldehyde (1.141 g, 6 mmol) and bromoform (0.630 mL, 7.20 mmol) in MeOH (5.00 mL) at 0° C. The mixture was then allowed to warm to r.t. and left to stir overnight. A white precipitate formed in the reaction mixture. The solids were filtered off under reduced pressure rinsing the filter cake with MeOH (15 mL). The filtrate was evaporated to a thick white paste then re-dissolved in water (50 mL). This was then washed with Et₂O (50 mL). The aqueous phase was acidified to pH=2 (~5 mL 2M HCl solution) and then extracted into EtOAc (3×50 mL). The combined organics were dried (MgSO₄), filtered and evaporated under reduced pressure to give a clear oil. The crude product was purified by FCC (SiO₂, 10-50% EtOAc in heptanes). Pure fractions were evaporated to dryness to afford 2-methoxy-2-[3-(trifluoromethoxy)phenyl]acetic acid (0.832 g, 55%) as a colourless oil. ¹H NMR (400 MHz, CDCl₃, 30° C.) δ 3.47 (3H, s), 4.81 (1H, s), 7.20-7.24 (1H, m), 7.33 (1H, s), 7.37-7.46 (2H, m). m/z: ES⁻ [M−H]⁻ 249.4.

Intermediate 20

2-[3-(Difluoromethoxy)phenyl]-2-methoxy-acetic acid

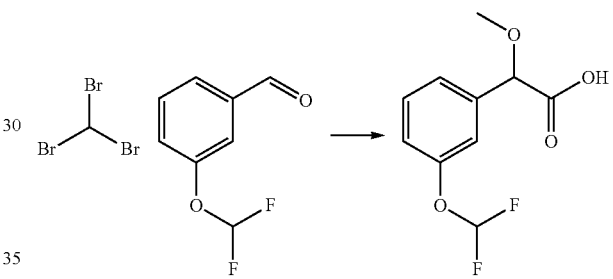

To a stirred mixture of 3-(difluoromethoxy)benzaldehyde (2.0 g, 11.61 mmol) and bromoform (1.22 mL, 13.94 mmol) in MeOH (40 mL) at 0° C. was added dropwise over a 1 hour period a solution of potassium hydroxide (3.59 g, 63.90 mmol) in MeOH (60 mL). After addition the mixture left to stir as it warmed to room temperature overnight. The precipitate was removed by filtration and the filtrate was evaporated to give a paste which was taken up in water (100 mL) and extracted with EtOAc (2×75 mL). The aqueous phase was then acidified to pH=1 with 2M HCl and extracted with EtOAc (2×75 mL). The combined organics were dried (MgSO₄), filtered, and evaporated to give a pale brown oil. This was purified by FCC (SiO₂, 95:5 cyclohexane: EtOAc+ 0.1% formic acid increasing to 8:2 EtOAc:cyclohexane+ 0.1% formic acid). Appropriate fractions were evaporated under reduced pressure to provide 2-[3-(difluoromethoxy)phenyl]-2-methoxy-acetic acid as a colourless oil (1.3 g 48%). ¹H NMR (400 MHz, CDCl₃, 21° C.) δ 3.46 (3H, s), 4.80 (1H, s), 6.53 (1H, t), 7.10-7.15 (1H, m), 7.22-7.23 (1H, m), 7.29-7.32 (1H, m), 7.39 (1H, t). m/z: ES⁻ [M−H]⁻ 231.

Intermediate 21

2-Methoxy-2-(4-methoxyphenyl)acetic acid

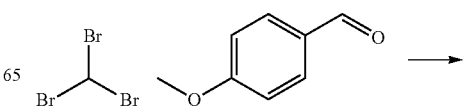

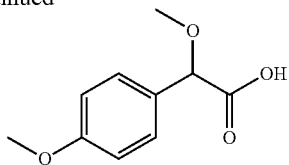

To a stirred mixture of p-anisaldehyde (3.58 g, 26.29 mmol) and bromoform (2.76 mL, 31.55 mmol) in MeOH (30 mL) at 0° C. was added, dropwise over 30 mins, a solution of potassium hydroxide (8.12 g, 144.65 mmol) in MeOH (60 mL). After the addition the mixture left to stir as it warmed to r.t. overnight. Next morning the precipitate was removed by filtration. The filtrate was evaporated to give a paste which was taken up in water (100 mL) and extracted with EtOAc (2×100 mL) to remove any remaining unreacted starting aldehyde. The aqueous phase was then acidified to pH=2 with 2N HCl. It was extracted with EtOAc (2×100 mL). The combined organics were dried (MgSO$_4$), filtered and evaporated to give 2-methoxy-2-(4-methoxyphenyl) acetic acid as an orange gum (3.1 g, 60%). $^1$H NMR (400 mHz, DMSO, 30° C.) 3.27 (3H, s), 3.75 (3H, s), 4.69 (1H, s), 6.93 (2H, d), 7.30 (2H, d), 12.45 (1H, brs). m/z: ES$^-$ [M−H]$^-$ 195.

Biological Assays

The following assays were used to measure the effects of the compounds described herein: a) GLS Enzyme Potency Assay; b) GLS Cell Potency Assay; c) GLS Cell Proliferation Assay. During the description of the assays, generally:
  i. The following abbreviations have been used: $CO_2$=Carbon dioxide; DMEM=Dulbecco's Modified Eagle Medium; DMSO=Dimethyl sulphoxide; EDTA=Ethylenediaminetetraacetic acid; EGTA=Ethylene glycol tetraacetic acid; FCS=Foetal calf serum; h=Hour(s); NBS=Non-binding surface; SDS=Sodium dodecyl sulphate; TRIS=Tris(Hydroxymethyl)aminomethane.
  ii. $IC_{50}$ values were calculated using a smart fitting model in Genedata. The $IC_{50}$ value was the concentration of test compound that inhibited 50% of biological activity.

Assay a): GLS Enzyme Potency Assay

A Glutamate Oxidase/AmplexRed coupled assay was used to measure the ability of compounds to bind to and inhibit the activity of GLS1 in vitro. 6His tagged GLS protein (amino acids 63-669) expressed in *E. Coli* was purified and stored at −80° C. in aliquots. GLS1 was diluted to 2× working concentration and incubated at room temperature to allow the tetrameric/dimeric forms to reach steady state. Assay measurements were performed in buffer comprising 50 mM TRIS pH 7.8, 100 mM NaPO$_4$, pH 7.8, 0.001% v/v Tween20. Purified recombinant GLS1 protein was diluted in assay buffer to 12 nM and pre-incubated at room temperature for 30 minutes. Test compounds were prepared by dilution in 100% DMSO to give the correct dose range for 12 point concentration response and an appropriate volume (2.5-60 nl) dispensed into 384 well micro assay plates (Greiner product code 784900) using a Labcyte Echo 555 acoustic dispenser. DMSO concentration was maintained at 2% by back filling with DMSO solution. 3 µL of diluted GLS1 protein (12 nM) was then dispensed into each well using a BioRaptr automated dispenser (Beckman-Coulter) and incubated for 15 minutes at room temperature. 3 µL of 100 mM glutamine diluted in assay buffer was then added and the reaction incubated at room temperature for 60 minutes. The reaction was then stopped by addition of 45 µM 6-(2-bromoethynyl)-2,3-dimethyl-quinazolin-4-one, 75 µM Amplex Red, 0.375 units/mL Horseradish Peroxidase, 0.12 units/mL Glutamate Oxidase in 100 mM TRIS pH7.5. After 30 minutes at room temp in the dark, plates were read on a Perkin Elmer EnVision using 535/590 nm optic filters and raw data analysed using Genedata to generate $IC_{50}$ values. An artefact version of the assay where the 6His tagged GLS protein and glutamine were replaced with assay buffer was also used to rule out non specific effects on the assay components.

Assay b): GLS Cell Potency Assay

Compounds were assessed for their potential to inhibit cellular GLS activity by use of a PC3 coupled assay measuring cellular glutamate depletion. Test compounds were prepared by dilution in 100% DMSO to give the correct dose range for 12 point concentration response and an appropriate volume (5-120 nl) dispensed into 384 well micro assay plates (Corning product code 3712) using a Labcyte Echo 555 acoustic dispenser. DMSO concentration was maintained at 0.3% by back filling with DMSO solution. PC3 cells were grown in phenol free DMEM, 10% dialyzed FCS, 2 mM glutamine and following dispersal by trypsinisation were plated at 5.6×10$^3$ cells per well in 40 µl of growth medium directly into the 384 well assay plates containing dispensed compound. After incubation for 6 h at 37° C., 5% $CO_2$ growth media was aspirated and cells lysed in 15 µl of buffer containing 10 mM TRIS pH7.4, 100 mM NaCl, 1 mM EDTA, 1 mM EGTA, 1 mM NaF, 20 mM Na$_4$P$_2$O$_7$, 2 mM Na$_3$VO$_4$, 1% Triton X-100, 10% glycerol, 0.1% SDS and 0.5% deoxycholate. 4 µl Of cell lysate was then transferred to a 384 well NBS plate (Corning product code 3575) and 35 µl of 27.5 µM Amplex Red, 0.1375 U/mL Horseradish Peroxidase, 0.044 U/mL glutamate oxidase, 100 mM TRIS pH7.5 was added. After 30 minutes at room temp in the dark, plates were read on a Perkin Elmer EnVision using 535/590 nm optic filters and raw data analysed using proprietary software to generate $IC_{50}$ values.

Assay c): GLS Cell Proliferation Assay

The ability of compounds to inhibit cell growth was measured using a 384 well plate NCI-H1703 cell proliferation assay. NCI-H1703 cells were grown in phenol red free RPMI1640, 10% FCS and 2 mM glutamine and seeded at a density of 750 cells per well in 40 µl of growth medium into clear-bottom 384 well assay plates (Corning product code 3712) and incubated for 24 h at 37° C., 5% $CO_2$. Test compounds were prepared by dilution in 100% DMSO to give the correct dose range for 12 point concentration response and an appropriate volume (5-120 nl) dispensed directly into the assay plates containing plated cells. DMSO concentration was maintained at 0.3% by back filling with DMSO solution. Plates were incubated for 5 days at 37° C., 5% $CO_2$, Sytox Green and Saponin added to final concentration of 2 µM and 0.25% respectively and incubated for 6 h prior to analysis. Plates were read on an Acumen eX3 (TTP Labtech) using 488 nm excitation and FITC filter set (500-530 nm) for emission. $IC_{50}$ values were calculated by curve fitting to max inhibition of day zero growth using GeneData software analysis.

Results from assays a)-c) are shown in Table 1.

TABLE 1

Assay data

| Example | Assay a) enz IC$_{50}$ µM | Assay b) GLS cell MOA Mean IC$_{50}$ µM | Assay c) Prolif Mean IC$_{50}$ µM |
|---|---|---|---|
| 1(a) | 0.0554 | 0.000566 | 0.00459 |
| 1(b) | 0.406 | 0.137 | 0.454 |
| 2 | 0.0303 | 0.000965 | 0.0167 |
| 3 | 0.0388 | 0.000384 | 0.00362 |
| 4(a) | 0.0792 | 0.000457 | 0.00664 |
| 4(b) | 0.29 | 0.0431 | 0.389 |
| 5(a) | 0.155 | 0.00278 | 0.0441 |
| 5(b) | 0.975 | — | 1.02 |
| 6(a) | 0.0827 | — | 0.0209 |
| 6(b) | 2.53 | 0.0736 | 0.926 |
| 7(a) | 0.0952 | 0.000556 | 0.00308 |
| 7(b) | 0.334 | 0.0127 | 0.0256 |
| 8(a) | 0.0994 | 0.0013 | 0.00548 |
| 8(b) | 0.643 | 0.0221 | 0.117 |
| 9(a) | 0.0227 | 0.00056 | 0.00309 |
| 9(b) | 0.0989 | 0.0185 | 0.469 |
| 10(a) | 0.0311 | 0.00105 | 1.21 |
| 10(b) | 0.241 | 0.0179 | 0.204 |
| 11(a) | 0.0159 | — | 0.0544 |
| 11(b) | 0.0848 | 0.0105 | 0.129 |
| 12 | 0.0353 | 0.000451 | 0.00307 |
| 13 | 0.0592 | 0.000658 | 0.00848 |
| 14 | 0.0443 | 0.00104 | 0.0227 |
| 15 | 0.277 | 0.0348 | 0.567 |
| 16 | 0.0809 | 0.00274 | 0.055 |
| 17 | 0.0243 | 0.000251 | 0.00174 |
| 18 | 0.0653 | 0.00491 | 0.0168 |
| 19 | 0.0557 | 0.0047 | 0.0719 |
| 20 | 0.323 | 0.0795 | 1.27 |
| 21 | 0.223 | 0.0537 | 0.93 |
| 22 | 0.0189 | 0.00245 | 0.0369 |
| 23 | 0.265 | 0.197 | 0.106 |
| 24 | 0.0713 | 0.00101 | 0.0116 |
| 25 | 1.09 | 0.0632 | 0.686 |
| 26 | 0.0948 | 0.00212 | 0.0219 |
| 27 | 2.38 | 0.0722 | 1.22 |
| 28 | 0.096 | 0.00357 | 0.0732 |
| 29 | 1.28 | — | 0.586 |
| 30 | 0.119 | 0.00529 | 0.0437 |
| 31 | 0.0592 | 0.000658 | 0.00848 |
| 32 | 0.0353 | 0.000451 | 0.00307 |
| 33(a) | 0.148 | 0.0192 | 0.0189 |
| 33(b) | 0.0799 | 0.00235 | 0.0379 |

The invention claimed is:

1. A compound of Formula (I):

(I)

[Chemical structure diagram]

or a pharmaceutically acceptable salt thereof, wherein:
Q is 5-methylpyridazin-3-yl, 5-chloropyridazin-3-yl, 6-methylpyridazin-3-yl, or 6-fluoropyridazin-3-yl;
R is hydrogen, fluoro, or methoxy;
R$^1$ is hydrogen, methoxy, difluoromethoxy, or trifluoromethoxy; and
R$^2$ is methyl or ethyl.

2. The compound of claim 1, or a pharmaceutically acceptable salt thereof, wherein Q is 6-methylpyridazin-3-yl, or 6-fluoropyridazin-3-yl.

3. The compound of claim 1, or a pharmaceutically acceptable salt thereof, wherein R is hydrogen or fluoro.

4. The compound of claim 1, or a pharmaceutically acceptable salt thereof, wherein R is hydrogen.

5. The compound of claim 1, or a pharmaceutically acceptable salt thereof, wherein R$^1$ is methoxy, difluoromethoxy, or trifluoromethoxy.

6. The compound of claim 1, or a pharmaceutically acceptable salt thereof, wherein R$^2$ is methyl.

7. The compound of claim 1, or a pharmaceutically acceptable salt thereof, where in the compound is selected from the group consisting of:
(2S)-2-methoxy-2-(3-methoxyphenyl)-N-[5-[[(3R)-1-(6-methylpyridazin-3-yl)pyrrolidin-3-yl]amino]-1,3,4-thiadiazol-2-yl]acetamide;
(2S)-N-[5-[[(3R)-1-(6-fluoropyridazin-3-yl)pyrrolidin-3-yl]amino]-1,3,4-thiadiazol-2-yl]-2-methoxy-2-phenyl-acetamide;
(2S)-N-[5-[[(3R)-1-(6-fluoropyridazin-3-yl)pyrrolidin-3-yl]amino]-1,3,4-thiadiazol-2-yl]-2-methoxy-2-(3-methoxyphenyl)acetamide;
(2S)-2-ethoxy-2-(3-methoxyphenyl)-N-[5-[[(3R)-1-(6-methylpyridazin-3-yl)pyrrolidin-3-yl]amino]-1,3,4-thiadiazol-2-yl]acetamide;
(2S)-2-(4-fluorophenyl)-2-methoxy-N-[5-[[(3R)-1-(6-methylpyridazin-3-yl)pyrrolidin-3-yl]amino]-1,3,4-thiadiazol-2-yl]acetamide;
(2S)-2-(4-fluoro-3-methoxy-phenyl)-2-methoxy-N-[5-[[(3R)-1-(6-methylpyridazin-3-yl)pyrrolidin-3-yl]amino]-1,3,4-thiadiazol-2-yl]acetamide;
(2S)-2-methoxy-N-[5-[[(3R)-1-(6-methylpyridazin-3-yl)pyrrolidin-3-yl]amino]-1,3,4-thiadiazol-2-yl]-2-[3-(trifluoromethoxy)phenyl]acetamide;
(2S)-2-(4-fluorophenyl)-2-methoxy-N-[5-[[(3R)-1-(5-methylpyridazin-3-yl)pyrrolidin-3-yl]amino]-1,3,4-thiadiazol-2-yl]acetamide;
N-[5-[[(3R)-1-(5-chloropyridazin-3-yl)pyrrolidin-3-yl]amino]-1,3,4-thiadiazol-2-yl]-2-methoxy-2-(4-methoxyphenyl)acetamide;
(2S)-[3-(difluoromethoxy)phenyl]-2-methoxy-N-[5-[[(3R)-1-(6-methylpyridazin-3-yl)pyrrolidin-3-yl]amino]-1,3,4-thiadiazol-2-yl]acetamide; and
(2S)-2-[3-(difluoromethoxy)phenyl]-N-[5-[[(3R)-1-(6-fluoropyridazin-3-yl)pyrrolidin-3-yl]amino]-1,3,4-thiadiazol-2-yl]-2-methoxy-acetamide.

8. The compound of claim 1, or a pharmaceutically acceptable salt thereof, wherein the compound is selected from the group consisting of:
(2S)-2-methoxy-2-(3-methoxyphenyl)-N-[5-[[(3R)-1-(6-methylpyridazin-3-yl)pyrrolidin-3-yl]amino]-1,3,4-thiadiazol-2-yl]acetamide;
(2S)-N-[5-[[(3R)-1-(6-fluoropyridazin-3-yl)pyrrolidin-3-yl]amino]-1,3,4-thiadiazol-2-yl]-2-methoxy-2-(3-methoxyphenyl)acetamide;
(2S)-2-ethoxy-2-(3-methoxyphenyl)-N-[5-[[(3R)-1-(6-methylpyridazin-3-yl)pyrrolidin-3-yl]amino]-1,3,4-thiadiazol-2-yl]acetamide;
(2S)-2-(4-fluorophenyl)-2-methoxy-N-[5-[[(3R)-1-(6-methylpyridazin-3-yl)pyrrolidin-3-yl]amino]-1,3,4-

(2S)-2-(4-fluoro-3-methoxy-phenyl)-2-methoxy-N-[5-[[(3R)-1-(6-methylpyridazin-3-yl)pyrrolidin-3-yl]amino]-1,3,4-thiadiazol-2-yl]acetamide;

(2S)-2-methoxy-N-[5-[[(3R)-1-(6-methylpyridazin-3-yl)pyrrolidin-3-yl]amino]-1,3,4-thiadiazol-2-yl]-2-[3-(trifluoromethoxy)phenyl]acetamide;

(2S)-2-(4-fluorophenyl)-2-methoxy-N-[5-[[(3R)-1-(5-methylpyridazin-3-yl)pyrrolidin-3-yl]amino]-1,3,4-thiadiazol-2-yl]acetamide;

(2S)-[3-(difluoromethoxy)phenyl]-2-methoxy-N-[5-[[(3R)-1-(6-methylpyridazin-3-yl)pyrrolidin-3-yl]amino]-1,3,4-thiadiazol-2-yl]acetamide; and (2S)-2-[3-(difluoromethoxy)phenyl]-N-[5-[[(3R)-1-(6-fluoropyridazin-3-yl)pyrrolidin-3-yl]amino]-1,3,4-thiadiazol-2-yl]-2-methoxy-acetamide.

9. A pharmaceutical composition comprising the compound of claim 1, or a pharmaceutically acceptable salt thereof, and at least one pharmaceutically acceptable diluent or carrier.

* * * * *